(12) United States Patent
Abraham et al.

(10) Patent No.: US 10,358,498 B2
(45) Date of Patent: Jul. 23, 2019

(54) HUMAN ANTI-FGFR4 ANTIBODY

(71) Applicants: Daiichi Sankyo Europe GmbH, Munich (DE); Daiichi Sankyo Company, Limited, Tokyo (JP)

(72) Inventors: Reimar Abraham, Munich (DE); Keisuke Fukuchi, Tokyo (JP); Tanja Lange, Germering (DE); Johannes Bange, Krailling (DE); Ichiro Watanabe, Tokyo (JP); Shinko Hayashi, Tokyo (JP); Toshiaki Ohtsuka, Tokyo (JP)

(73) Assignees: Daiichi Sankyo Europe GmbH, Munich (DE); Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 15/503,095

(22) PCT Filed: Aug. 11, 2015

(86) PCT No.: PCT/EP2015/068440
§ 371 (c)(1),
(2) Date: Feb. 10, 2017

(87) PCT Pub. No.: WO2016/023894
PCT Pub. Date: Feb. 18, 2016

(65) Prior Publication Data
US 2017/0226213 A1    Aug. 10, 2017

(30) Foreign Application Priority Data
Aug. 11, 2014   (EP) .................... 14180555

(51) Int. Cl.
*A61K 39/00*    (2006.01)
*C07K 16/28*    (2006.01)
*C07K 16/32*    (2006.01)

(52) U.S. Cl.
CPC ......... *C07K 16/2863* (2013.01); *C07K 16/32* (2013.01); *A61K 2039/505* (2013.01); *C07K 2317/56* (2013.01); *C07K 2317/565* (2013.01); *C07K 2317/76* (2013.01); *C07K 2317/92* (2013.01)

(58) Field of Classification Search
CPC ............... C07K 16/2863; C07K 16/32; C07K 2317/565; C07K 2317/56; C07K 2317/76; A61K 2039/505
See application file for complete search history.

(56) References Cited

U.S. PATENT DOCUMENTS

2011/0150903 A1*  6/2011  Baurin ............... C07K 16/2863
                                              424/158.1

FOREIGN PATENT DOCUMENTS

| WO | 2010004204 | 1/2010 |
| WO | 2012138975 | 11/2012 |

OTHER PUBLICATIONS

Rudikoff et al., Single amino acid substitution altering antigen-binding specificity. Proc. Natl. Acad. Sci. USA 79:1979-1983, 1982.*
French, et al. "Targeting FGFR4 Inhibits Hepatocellular Carcinoma in Preclinical Mouse Models", PLos ONE, vol. 7, No. 5, May 2012, pp. 1-12.
Chen, et al., "Generation and Characterization of a Panel of Monoclonal Antibodies Specific for Human Fibroblast Growth Factor Receptor 4 (FGFR4)", Hybridoma, vol. 23, No. 3, 2005. pp. 152-159.

* cited by examiner

*Primary Examiner* — Ruixiang Li
(74) *Attorney, Agent, or Firm* — Withers & Keys, LLC

(57) ABSTRACT

The present invention relates to novel antibodies against the FGF receptor 4 (FGFR4) and to the medical use thereof, in particular for the diagnosis prevention or treatment of diseases associated with FGFR expression, over expression or hyperactivity.

10 Claims, 23 Drawing Sheets
Specification includes a Sequence Listing.

(A)

(B)

Figure 11
(A)
Immunoprecipitation: FGFR4
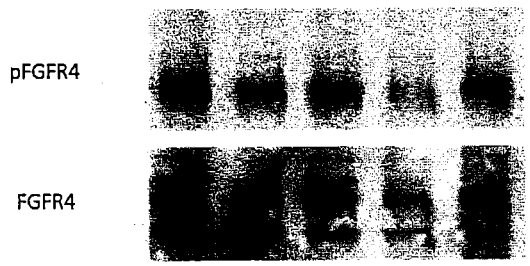
| Lane | 1 | 2 | 3 | 4 | 5 |
|---|---|---|---|---|---|
| Antibody | U4-3 | U4-3 | U4-3 | U4-3 | IgG ctrl. |
| Concentration [µg/ml] | 0.3 | 1 | 3 | 10 | 1 |
pFGFR4
FGFR4
(B)
Whole Cell Lysates
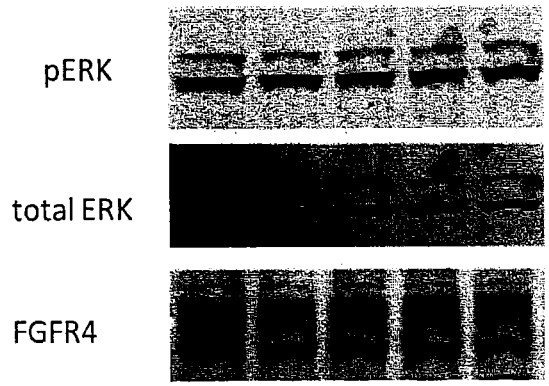
| Lane | 1 | 2 | 3 | 4 | 5 |
|---|---|---|---|---|---|
| Antibody | U4-3 | U4-3 | U4-3 | U4-3 | IgG ctrl. |
| Concentration [µg/ml] | 0.3 | 1 | 3 | 10 | 1 |
pERK
total ERK
FGFR4

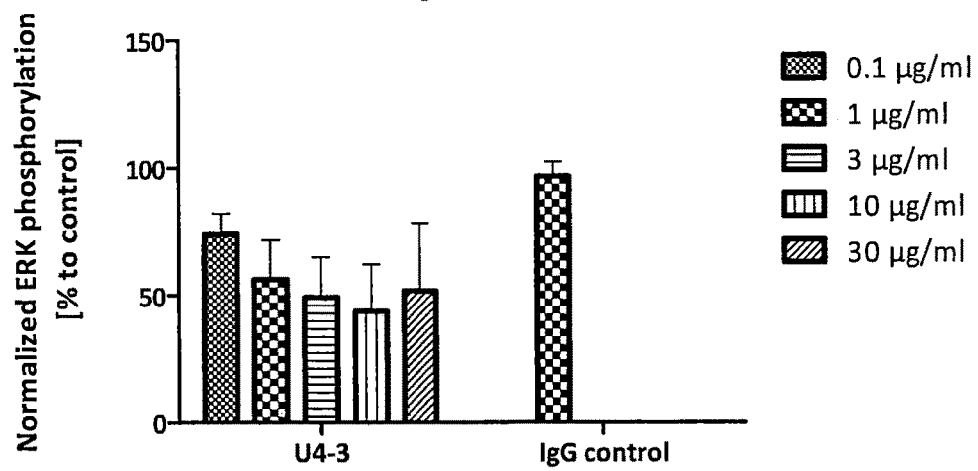

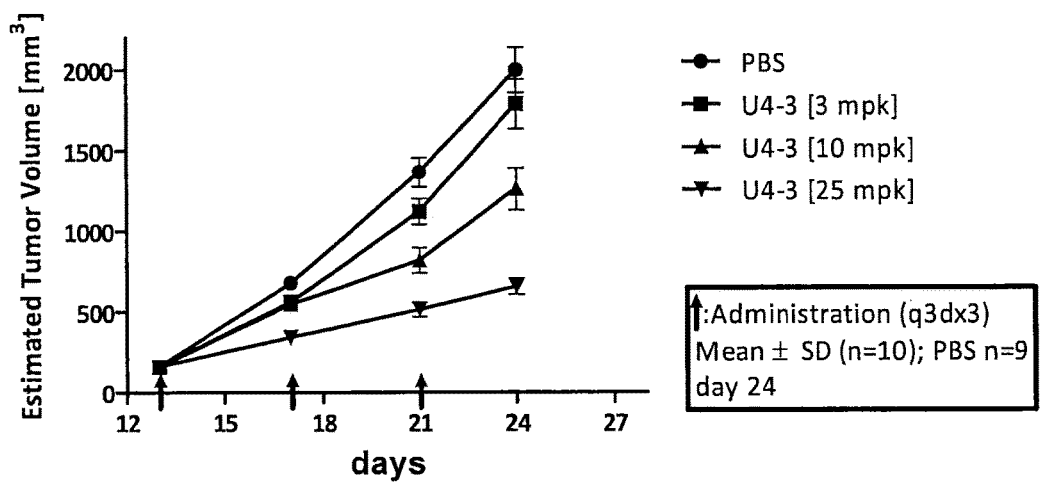
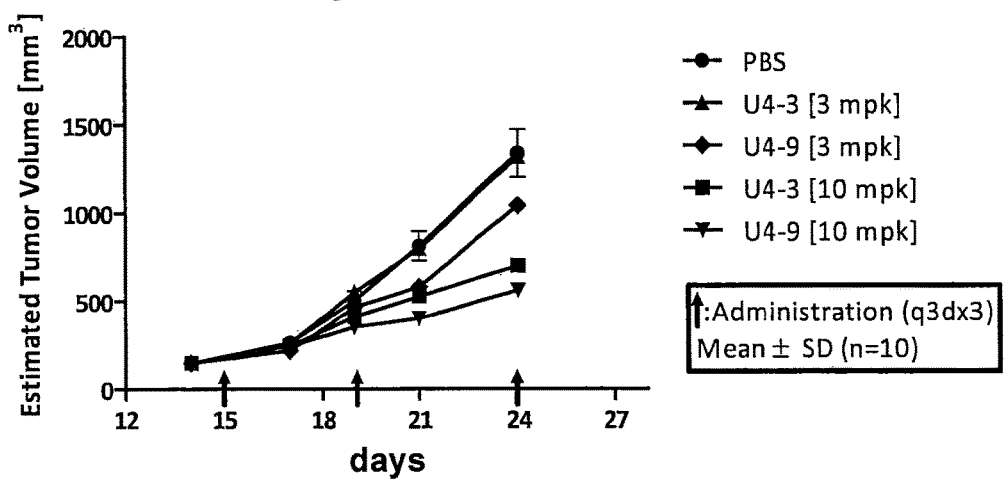

SEQUENCE LISTING

<160> NUMBER OF SEQ ID NOS: 68

<210> SEQ ID NO 1
<211> LENGTH: 5
<212> TYPE: PRT
<213> ORGANISM: Artificial Sequence
<220> FEATURE:
<223> OTHER INFORMATION: U4-1-VH CDRH1

<400> SEQUENCE: 1

Arg Asn Tyr Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: U4-2-VH CDRH1

<400> SEQUENCE: 2

Lys Ala Trp Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: U4-3-VH, U4-7-VH and U4-9-VH CDRH1

<400> SEQUENCE: 3

Asp Tyr Tyr Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: U4-4-VH and U4-8-VH CDRH1

<400> SEQUENCE: 4

Ser Asn Tyr Met Ser
1               5

<210> SEQ ID NO 5
<211> LENGTH: 5
<212> TYPE: PRT
<213> ORGANISM: Artificial Sequence
<220> FEATURE:
<223> OTHER INFORMATION: U4-5-VH CDRH1

<400> SEQUENCE: 5

Ser Asn Tyr Met Asn
1               5

<210> SEQ ID NO 6
<211> LENGTH: 5
<212> TYPE: PRT
<213> ORGANISM: Artificial Sequence
<220> FEATURE:
<223> OTHER INFORMATION: U4-6-VH CDRH1

<400> SEQUENCE: 6

Asp Tyr Tyr Met Asn
1               5

<210> SEQ ID NO 7
<211> LENGTH: 17
<212> TYPE: PRT
<213> ORGANISM: Artificial Sequence
<220> FEATURE:
<223> OTHER INFORMATION: U4-1-VH, U4-2-VH and U4-7-VH CDRH2

<400> SEQUENCE: 7

Ala Ile Ser Gly Ser Gly Gly Ser Thr Tyr Tyr Ala Asp Ser Val Lys
 1               5                  10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: U4-3-VH and U4-9-VH CDRH2

<400> SEQUENCE: 8

Thr Ile Ser Gly Ser Gly Gly Ser Thr Tyr Tyr Ala Asp Ser Val Lys
 1               5                  10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: U4-4-VH CDRH2

<400> SEQUENCE: 9

Leu Ile Ser Gly Ser Gly Gly Ser Thr Tyr Tyr Ala Asp Ser Val Gln
 1               5                  10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: U4-5-VH CDRH2

<400> SEQUENCE: 10

Val Ile Ser Tyr Asp Gly Ser Asn Lys Tyr Tyr Ala Asp Ser Val Lys
 1               5                  10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: U4-8-VH CDRH2

<400> SEQUENCE: 11

Ser Ile Ser Gly Ser Gly Gly Arg Thr Tyr Tyr Ala Asp Ser Val Lys
 1               5                  10                  15

Gly

<210> SEQ ID NO 12
<211> LENGTH: 17

```
<212> TYPE: PRT
<213> ORGANISM: Artificial Sequence
<220> FEATURE:
<223> OTHER INFORMATION: U4-6-VH CDRH2

<400> SEQUENCE: 12

Ala Ile Gly Gly Ser Gly Asp Arg Thr Tyr Tyr Ala Asp Ser Val Lys
1               5                   10                  15
Gly

<210> SEQ ID NO 13
<211> LENGTH: 9
<212> TYPE: PRT
<213> ORGANISM: Artificial Sequence
<220> FEATURE:
<223> OTHER INFORMATION: U4-1-VH CDRH3

<400> SEQUENCE: 13

Val Thr Ser Pro Gly Ala Phe Asp Ile
1               5

<210> SEQ ID NO 14
<211> LENGTH: 9
<212> TYPE: PRT
<213> ORGANISM: Artificial Sequence
<220> FEATURE:
<223> OTHER INFORMATION: U4-2-VH CDRH3

<400> SEQUENCE: 14

Leu Tyr Ser Tyr Gly Asp Phe Asp His
1               5

<210> SEQ ID NO 15
<211> LENGTH: 9
<212> TYPE: PRT
<213> ORGANISM: Artificial Sequence
<220> FEATURE:
<223> OTHER INFORMATION: U4-3-VH and U4-9-VH CDRH3

<400> SEQUENCE: 15

Leu Thr Ala Tyr Gly His Val Asp Ser
1               5

<210> SEQ ID NO 16
<211> LENGTH: 10
<212> TYPE: PRT
<213> ORGANISM: Artificial Sequence
<220> FEATURE:
<223> OTHER INFORMATION: U4-4-VH CDRH3

<400> SEQUENCE: 16

Asn Thr Ala Gly Phe Gly Tyr Phe Asp Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: U4-5-VH CDRH3

<400> SEQUENCE: 17

Lys Ser Arg Asp Phe Trp Arg Gly Pro Phe Asp Tyr
1               5                   10

<210> SEQ ID NO 18
```

```
<211> LENGTH: 9
<212> TYPE: PRT
<213> ORGANISM: Artificial Sequence
<220> FEATURE:
<223> OTHER INFORMATION: U4-8-VH CDRH3

<400> SEQUENCE: 18

Met Thr Val Phe Gly Ala Ala Thr Leu
1               5

<210> SEQ ID NO 19
<211> LENGTH: 7
<212> TYPE: PRT
<213> ORGANISM: Artificial Sequence
<220> FEATURE:
<223> OTHER INFORMATION: U4-6-VH CDRH3

<400> SEQUENCE: 19

Gly Gly Ser Tyr Phe Gly Tyr
1               5

<210> SEQ ID NO 20
<211> LENGTH: 9
<212> TYPE: PRT
<213> ORGANISM: Artificial Sequence
<220> FEATURE:
<223> OTHER INFORMATION: U4-7-VH CDRH3

<400> SEQUENCE: 20

Leu Ala Thr Tyr Gly Pro Phe Asp Asp
1               5

<210> SEQ ID NO 21
<211> LENGTH: 13
<212> TYPE: PRT
<213> ORGANISM: Artificial Sequence
<220> FEATURE:
<223> OTHER INFORMATION: U4-1-VL CDRL1

<400> SEQUENCE: 21

Ser Gly Gly Thr Ser Asn Ile Gly Thr Asn Thr Val Asn
1               5                   10

<210> SEQ ID NO 22
<211> LENGTH: 13
<212> TYPE: PRT
<213> ORGANISM: Artificial Sequence
<220> FEATURE:
<223> OTHER INFORMATION: U4-2-VL, U4-4-VL, U4-5-VL, U4-6-VL and U4-8-VL
      CDRL1

<400> SEQUENCE: 22

Ser Gly Ser Ser Ser Asn Ile Gly Ser Asn Thr Val Asn
1               5                   10

<210> SEQ ID NO 23
<211> LENGTH: 13
<212> TYPE: PRT
<213> ORGANISM: Artificial Sequence
<220> FEATURE:
<223> OTHER INFORMATION: U4-3-VL CDRL1

<400> SEQUENCE: 23

Ser Gly Ser Ser Ser Asn Ile Gly Thr Asn Thr Val Asn
1               5                   10

<210> SEQ ID NO 24
```

```
<211> LENGTH: 7
<212> TYPE: PRT
<213> ORGANISM: Artificial Sequence
<220> FEATURE:
<223> OTHER INFORMATION: U4-1-VL, U4-2-VL, U4-4-VL, U4-5-VL and U4-8-VL
      CDRL2

<400> SEQUENCE: 24

Arg Asn Asn Gln Arg Pro Ser
1               5

<210> SEQ ID NO 25
<211> LENGTH: 7
<212> TYPE: PRT
<213> ORGANISM: Artificial Sequence
<220> FEATURE:
<223> OTHER INFORMATION: U4-3-VL CDRL2

<400> SEQUENCE: 25

Arg Asn Tyr Gln Arg Pro Ser
1               5

<210> SEQ ID NO 26
<211> LENGTH: 7
<212> TYPE: PRT
<213> ORGANISM: Artificial Sequence
<220> FEATURE:
<223> OTHER INFORMATION: U4-6-VL CDRL2

<400> SEQUENCE: 26

Tyr Asp Asp Leu Leu Pro Ser
1               5

<210> SEQ ID NO 27
<211> LENGTH: 7
<212> TYPE: PRT
<213> ORGANISM: Artificial Sequence
<220> FEATURE:
<223> OTHER INFORMATION: U4-7-VL and U4-9-VL CDRL2

<400> SEQUENCE: 27

Arg Asn Asn Arg Arg Pro Ser
1               5

<210> SEQ ID NO 28
<211> LENGTH: 13
<212> TYPE: PRT
<213> ORGANISM: Artificial Sequence
<220> FEATURE:
<223> OTHER INFORMATION: U4-1-VL CDRL3

<400> SEQUENCE: 28

Ala Ala Trp Asp Asp Ser Leu Asn Gly Pro Tyr Val Val
1               5                   10

<210> SEQ ID NO 29
<211> LENGTH: 13
<212> TYPE: PRT
<213> ORGANISM: Artificial Sequence
<220> FEATURE:
<223> OTHER INFORMATION: U4-2-VL CDRL3

<400> SEQUENCE: 29

Ala Ala Trp Asp Asp Ser Leu Asn Gly Pro Ala Val Val
1               5                   10

<210> SEQ ID NO 30
```

```
<211> LENGTH: 13
<212> TYPE: PRT
<213> ORGANISM: Artificial Sequence
<220> FEATURE:
<223> OTHER INFORMATION: U4-3-VL CDRL3

<400> SEQUENCE: 30

Ala Ala Trp Asp Asp Ser Leu Ser Gly Pro His Val Val
 1               5                  10

<210> SEQ ID NO 31
<211> LENGTH: 13
<212> TYPE: PRT
<213> ORGANISM: Artificial Sequence
<220> FEATURE:
<223> OTHER INFORMATION: U4-4-VL CDRL3

<400> SEQUENCE: 31

Ala Ala Trp Asp Asp Ser Leu Asn Gly Pro Leu Val Val
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: U4-5-VL CDRL3

<400> SEQUENCE: 32

Ser Thr Trp Asp Asp Ser Leu Arg Gly Trp Val
 1               5                  10

<210> SEQ ID NO 33
<211> LENGTH: 13
<212> TYPE: PRT
<213> ORGANISM: Artificial Sequence
<220> FEATURE:
<223> OTHER INFORMATION: U4-8-VL CDRL3

<400> SEQUENCE: 33

Ala Ala Trp Asp Asp Ser Leu Asn Gly Pro Tyr Trp Val
 1               5                  10

<210> SEQ ID NO 34
<211> LENGTH: 11
<212> TYPE: PRT
<213> ORGANISM: Artificial Sequence
<220> FEATURE:
<223> OTHER INFORMATION: U4-6-VL CDRL3

<400> SEQUENCE: 34

Ala Ala Trp Asp Asp Ser Leu Asn Gly Pro Val
 1               5                  10

<210> SEQ ID NO 35
<211> LENGTH: 13
<212> TYPE: PRT
<213> ORGANISM: Artificial Sequence
<220> FEATURE:
<223> OTHER INFORMATION: U4-7-VL and U4-9-VL CDRL3

<400> SEQUENCE: 35

Ala Ala Trp Asp Asp Ser Leu Ser Gly Pro Asn Val Val
 1               5                  10

<210> SEQ ID NO 36
<211> LENGTH: 354
```

```
<212> TYPE: DNA
<213> ORGANISM: Artificial Sequence
<220> FEATURE:
<223> OTHER INFORMATION: U4-1-VH

<400> SEQUENCE: 36
gaggtgcagc tgttggagtc tgggggaggc ttggtacagc ctgggggtc  cctgagactc    60 tcctgtgcag cctctggatt caccttcagt agaaactaca tgagttgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac actgccgtgt attactgtgc gagagttacc   300
tcaccagggg cttttgatat ctggggccaa ggtaccctgg tcaccgtgag ctca         354

<210> SEQ ID NO 37
<211> LENGTH: 399
<212> TYPE: DNA
<213> ORGANISM: Artificial Sequence
<220> FEATURE:
<223> OTHER INFORMATION: U4-2-VH

<400> SEQUENCE: 37
gaggtgcagc tgttggagtc tgggggaggc ttggtacagc ctgggggtc  cctgagactc    60 tcctgtgcag cctctggatt caccttcagt aaagcctgga tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac actgccgtgt attactgtgc gagattatac   300
agctatggtg actttgacca ctggggccaa ggtaccctgg tcaccgtgag ctcagcctcc   360
accaagggcc caagcgtctt ccccctggca cctcctcc                           399

<210> SEQ ID NO 38
<211> LENGTH: 399
<212> TYPE: DNA
<213> ORGANISM: Artificial Sequence
<220> FEATURE:
<223> OTHER INFORMATION: U4-3-VH and U4-9-VH

<400> SEQUENCE: 38
gaggtgcagc tgttggagtc tgggggaggc ttggtacagc ctgggggtc  cctgagactc    60 tcctgtgcag cctctggatt caccttcagt gactactaca tgagctggat ccgccaggct   120
ccagggaagg ggctggagtg ggtctcaact attagtggta gtggtggtag tacatactac   180
gcagactccg tgaagggccg gttcaccatc tccagagaca attccaagaa cacgctgtat   240
ctgcaaatga acagcctgag agccgaggac actgccgtgt attactgtgc cagactcacc   300
gcctatggcc acgtagactc ctggggccaa ggtaccctgg tcaccgtgag ctcagcctcc   360
accaagggcc caagcgtctt ccccctggca cctcctcc                           399

<210> SEQ ID NO 39
<211> LENGTH: 402
<212> TYPE: DNA
<213> ORGANISM: Artificial Sequence
<220> FEATURE:
<223> OTHER INFORMATION: U4-4-VH

<400> SEQUENCE: 39
gaggtgcagc tgttggagtc tgggggaggc ttggtacagc ctgggggtc  cctgagactc    60
```

| | |
|---|---:|
| tcctgtgcag cctctggatt caccttcagt agcaactaca tgagctgggt ccgccaggct | 120 |
| ccagggaagg ggctggagtg ggtctcactt attagtggta gtggtggtag cacatactac | 180 |
| gcagactccg tgcagggccg cttcaccatc tccagagaca attccaagaa cacgctgtat | 240 |
| ctgcaaatga acagcctgag agccgaggac actgccgtgt attactgtgc gagaaatacg | 300 |
| gctggttttg ggtacttcga tctctggggc caaggtaccc tggtcaccgt gagctcagcc | 360 |
| tccaccaagg gcccaagcgt cttccccctg gcaccctcct cc | 402 |

<210> SEQ ID NO 40
<211> LENGTH: 408
<212> TYPE: DNA
<213> ORGANISM: Artificial Sequence
<220> FEATURE:
<223> OTHER INFORMATION: U4-5-VH

<400> SEQUENCE: 40

| | |
|---|---:|
| gaggtgcagc tgttggagtc tgggggaggc ttggtacagc ctgggggtc cctgagactc | 60 |
| tcctgtgcag cctctggatt caccttcagt agcaactaca tgaactgggt ccgccaggct | 120 |
| ccagggaagg ggctggagtg ggtggcagtt atatcatatg atggaagtaa taaatactac | 180 |
| gcagactccg tgaagggccg attcaccatc tccagagaca attccaagaa cacgctgtat | 240 |
| ctgcaaatga acagcctgag agccgaggac actgccgtgt attactgtgt gacaaagtct | 300 |
| cgagattttt ggcggggtcc ctttgactac tggggccaag gtaccctggt caccgtgagc | 360 |
| tcagcctcca ccaagggccc aagcgtcttc cccctggcac cctcctcc | 408 |

<210> SEQ ID NO 41
<211> LENGTH: 399
<212> TYPE: DNA
<213> ORGANISM: Artificial Sequence
<220> FEATURE:
<223> OTHER INFORMATION: U4-8-VH

<400> SEQUENCE: 41

| | |
|---|---:|
| gaggtgcagc tgttggagtc tgggggaggc ttggtacagc ctgggggtc cctgagactc | 60 |
| tcctgtgcag cctctggatt caccttcagt agcaactaca tgagctgggt ccgccaggct | 120 |
| ccagggaagg ggctggagtg ggtctcaagt attagtggta gtggtggtcg cacatactac | 180 |
| gcagactccg tgaagggccg attcaccatc tccagagaca attccaagaa cacgctgtat | 240 |
| ctgcaaatga acagcctgag agccgaggac actgccgtgt attactgtgc gagaatgacg | 300 |
| gtctttggag cggcaacgct ctggggccaa ggtaccctgg tcaccgtgag ctcagcctcc | 360 |
| accaagggcc caagcgtctt ccccctggca ccctcctcc | 399 |

<210> SEQ ID NO 42
<211> LENGTH: 393
<212> TYPE: DNA
<213> ORGANISM: Artificial Sequence
<220> FEATURE:
<223> OTHER INFORMATION: U4-6-VH

<400> SEQUENCE: 42

| | |
|---|---:|
| gaggtgcagc tgttggagtc tgggggaggc ttggtacagc ctgggggtc cctgagactc | 60 |
| tcctgtgcag cctctggatt caccttcagt gactactaca tgaactgggt ccgccaggct | 120 |
| ccaggcaagg ggctggagtg ggtctcagct attggtggta gtggtgatag aacatactac | 180 |
| gcagactccg tgaagggccg gttcaccatc tccagagaca attccaagaa cacgctgtat | 240 |
| ctgcaaatga acagcctgag agccgaggac actgccgtgt attactgtgc tctcggtggg | 300 |

```
agctacttcg gctactgggg ccaaggtacc ctggtcaccg tgagctcagc ctccaccaag    360
ggcccaagcg tcttcccect ggcaccctcc tcc                                 393
```

<210> SEQ ID NO 43
<211> LENGTH: 399
<212> TYPE: DNA
<213> ORGANISM: Artificial Sequence
<220> FEATURE:
<223> OTHER INFORMATION: U4-7-VH

<400> SEQUENCE: 43

```
gaggtgcagc tgttggagtc tgggggaggc ttggtacagc ctgggggtc cctgagactc     60 tcctgtgcag cctctggatt caccttcagt gactactaca tgagctgggt ccgccaggct    120
cccgggaagg gctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac actgccgtgt attactgtgc gaccctggcc    300
acctacggac catttgacga ctggggccaa ggtaccctgg tcaccgtgag ctcagcctcc    360
accaagggcc caagcgtctt ccccctggca cctcctcc                           399
```

<210> SEQ ID NO 44
<211> LENGTH: 345
<212> TYPE: DNA
<213> ORGANISM: Artificial Sequence
<220> FEATURE:
<223> OTHER INFORMATION: U4-1-VL

<400> SEQUENCE: 44

```
cagtctgtgc tgactcagcc accctcagcg tctgggaccc ccgggcagag ggtcaccatc    60
tcttgttctg gaggcacctc caacatcgga actaatactg taaactggta tcagcagctc    120
ccaggaacgg cccccaaact cctcatctat aggaataatc agcggccctc agggggtccct   180 gaccgattct ctggctccaa gtctggcacc tcatcctccc tggccatcag tgggctccgg    240
tccgaggatg aggctgatta ttactgtgca gcatgggatg acagcctgaa tggtccctat    300
gtggtattcg gcggaggaac caagctgacg gtcctaggtc agcct                    345
```

<210> SEQ ID NO 45
<211> LENGTH: 345
<212> TYPE: DNA
<213> ORGANISM: Artificial Sequence
<220> FEATURE:
<223> OTHER INFORMATION: U4-2-VL

<400> SEQUENCE: 45

```
cagtctgtgc tgactcagcc accctcagcg tctgggaccc ccgggcagag ggtcaccatc    60
tcttgttctg gaagcagctc caacatcgga agtaatactg taaactggta tcagcagctc    120
ccaggaacgg cccccaaact cctcatctat cggaataatc agcggccctc agggggtccct   180 gaccgattct ctggctccaa gtctggcacc tcagcctccc tggccatcag tgggctccgg    240
tccgaggatg aggctgatta ttactgtgca gcatgggatg acagcctgaa tggtcccgct    300
gtggtattcg gcggaggaac caagctgacg gtcctaggtc agcct                    345
```

<210> SEQ ID NO 46
<211> LENGTH: 345
<212> TYPE: DNA
<213> ORGANISM: Artificial Sequence
<220> FEATURE:

<223> OTHER INFORMATION: U4-3-VL

<400> SEQUENCE: 46

```
cagtctgtgc tgactcagcc accctcagcg tctgggaccc ccgggcagag ggtcaccatc    60
tcttgttctg gaagcagctc caacatcgga actaatactg tgaactggta tcagcagctc   120
ccaggaacgg cccccaaact cctcatctat aggaattatc agagaccctc aggggtccct   180
gaccgattct ctggctccaa gtctggcacc tcagcctccc tggccatcag tgggctccgg   240
tccgaggatg aggctgatta ttactgtgca gcatgggatg atagcctgag tggtccacat   300
gtggtattcg gcggaggaac caagctgacg gtcctaggtc agcct                   345
```

<210> SEQ ID NO 47
<211> LENGTH: 345
<212> TYPE: DNA
<213> ORGANISM: Artificial Sequence
<220> FEATURE:
<223> OTHER INFORMATION: U4-4-VL

<400> SEQUENCE: 47

```
cagtctgtgc tgactcagcc accctcagcg tctgggaccc ccgggcagag ggtcaccatc    60
tcttgttctg gaagcagctc caacatcgga agtaatactg taaactggta tcagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgaa tggtccccta   300
gtggtattcg gcggaggaac caagctgacg gtcctaggtc agcct                   345
```

<210> SEQ ID NO 48
<211> LENGTH: 339
<212> TYPE: DNA
<213> ORGANISM: Artificial Sequence
<220> FEATURE:
<223> OTHER INFORMATION: U4-5-VL

<400> SEQUENCE: 48

```
cagtctgtgc tgactcagcc accctcagcg tctgggaccc ccgggcagag ggtcaccatc    60
tcttgttctg gaagcagctc caacatcgga agtaatactg taaactggta tcagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgttca acgtgggatg acagcctgag aggttgggtg   300
ttcggcggag gaaccaagct gacggtccta ggtcagcct                          339
```

<210> SEQ ID NO 49
<211> LENGTH: 345
<212> TYPE: DNA
<213> ORGANISM: Artificial Sequence
<220> FEATURE:
<223> OTHER INFORMATION: U4-8-VL

<400> SEQUENCE: 49

```
cagtctgtgc tgactcagcc accctcagca tctgggaccc ccgggcagag ggtcaccatc    60
tcttgttctg gaagcagctc caacatcgga agtaatactg taaactggta tcagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgaa tggtccctat   300
```
tgggtgttcg gcggaggaac caagctgacg gtcctaggtc agcct         345

<210> SEQ ID NO 50
<211> LENGTH: 339
<212> TYPE: DNA
<213> ORGANISM: Artificial Sequence
<220> FEATURE:
<223> OTHER INFORMATION: U4-6-VL

<400> SEQUENCE: 50
cagtctgtgc tgactcagcc accctcagcg tctgggaccc ccgggcagag ggtcaccatc    60
tcttgttctg gaagcagctc caacatcgga agtaatactg taaactggta tcagcagctc   120
ccaggaacgg cccccaaact cctcatctat tatgatgatc tgctgccctc aggggtccct   180
gaccgattct ctggctccaa gtctggcacc tcagcctccc tggccatcag tgggctccgg   240
tccgaggatg aggctgatta ttactgtgca gcatgggatg acagcctgaa tggtccggtg   300
ttcggcggag gaaccaagct gacggtccta ggtcagcct                          339

<210> SEQ ID NO 51
<211> LENGTH: 345
<212> TYPE: DNA
<213> ORGANISM: Artificial Sequence
<220> FEATURE:
<223> OTHER INFORMATION: U4-7-VL and U4-9-VL

<400> SEQUENCE: 51
cagtctgtgc tgactcagcc accctcagcg tctgggaccc ccgggcagag ggtcaccatc    60
tcttgttctg gaagcagctc caacatcgga agtaatactg tacactggta tcagcagctc   120
ccaggaacgg cccccaaact cctcatctat agaaataatc ggcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tggtccgaat   300
gtggtattcg gcggaggaac caagctgacg gtcctaggtc agcct                   345

<210> SEQ ID NO 52
<211> LENGTH: 118
<212> TYPE: PRT
<213> ORGANISM: Artificial Sequence
<220> FEATURE:
<223> OTHER INFORMATION: U4-1-VH

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Ser Pro Gly Ala Phe Asp Ile Trp Gly Gln Gly Thr
            100                 105                 110

Leu Val Thr Val Ser Ser

```
<210> SEQ ID NO 53
<211> LENGTH: 133
<212> TYPE: PRT
<213> ORGANISM: Artificial Sequence
<220> FEATURE:
<223> OTHER INFORMATION: U4-2-VH

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Ala
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Ser Tyr Gly Asp Phe Asp His Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
        130

<210> SEQ ID NO 54
<211> LENGTH: 133
<212> TYPE: PRT
<213> ORGANISM: Artificial Sequence
<220> FEATURE:
<223> OTHER INFORMATION: U4-3-VH and U4-9-VH

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Thr Ala Tyr Gly His Val Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
        130

<210> SEQ ID NO 55
<211> LENGTH: 134
```

<212> TYPE: PRT
<213> ORGANISM: Artificial Sequence
<220> FEATURE:
<223> OTHER INFORMATION: U4-4-VH

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Leu Ile Ser Gly Ser Gly Ser Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Thr Ala Gly Phe Gly Tyr Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser
    130

<210> SEQ ID NO 56
<211> LENGTH: 136
<212> TYPE: PRT
<213> ORGANISM: Artificial Sequence
<220> FEATURE:
<223> OTHER INFORMATION: U4-5-VH

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Thr Lys Ser Arg Asp Phe Trp Arg Gly Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser
    130                 135

<210> SEQ ID NO 57
<211> LENGTH: 133
<212> TYPE: PRT
<213> ORGANISM: Artificial Sequence
<220> FEATURE:
<223> OTHER INFORMATION: U4-8-VH

```
<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Ser Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Thr Val Phe Gly Ala Ala Thr Leu Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
        130

<210> SEQ ID NO 58
<211> LENGTH: 131
<212> TYPE: PRT
<213> ORGANISM: Artificial Sequence
<220> FEATURE:
<223> OTHER INFORMATION: U4-6-VH

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ser Ala Ile Gly Gly Ser Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Gly Gly Ser Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser
    130

<210> SEQ ID NO 59
<211> LENGTH: 133
<212> TYPE: PRT
<213> ORGANISM: Artificial Sequence
<220> FEATURE:
<223> OTHER INFORMATION: U4-7-VH

<400> SEQUENCE: 59

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Thr Tyr Gly Pro Phe Asp Asp Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
        130

<210> SEQ ID NO 60
<211> LENGTH: 115
<212> TYPE: PRT
<213> ORGANISM: Artificial Sequence
<220> FEATURE:
<223> OTHER INFORMATION: U4-1-VL

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Gly Thr Ser Asn Ile Gly Thr Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Tyr Val Val Phe Gly Gly Gly Thr Lys Leu Thr Val Leu
            100                 105                 110

Gly Gln Pro
        115

<210> SEQ ID NO 61
<211> LENGTH: 115
<212> TYPE: PRT
<213> ORGANISM: Artificial Sequence
<220> FEATURE:
<223> OTHER INFORMATION: U4-2-VL

<400> SEQUENCE: 61

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60
```

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Pro Ala Val Val Phe Gly Gly Gly Thr Lys Leu Thr Val Leu
            100                 105                 110

Gly Gln Pro
        115

<210> SEQ ID NO 62
<211> LENGTH: 115
<212> TYPE: PRT
<213> ORGANISM: Artificial Sequence
<220> FEATURE:
<223> OTHER INFORMATION: U4-3-VL

<400> SEQUENCE: 62

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Thr Asn
             20                  25                  30

Thr Val Asn Trp Tyr Gln Gln Leu Pro Gly Thr Ala Pro Lys Leu Leu
             35                  40                  45

Ile Tyr Arg Asn Tyr Gln Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Pro His Val Val Phe Gly Gly Gly Thr Lys Leu Thr Val Leu
            100                 105                 110

Gly Gln Pro
        115

<210> SEQ ID NO 63
<211> LENGTH: 115
<212> TYPE: PRT
<213> ORGANISM: Artificial Sequence
<220> FEATURE:
<223> OTHER INFORMATION: U4-4-VL

<400> SEQUENCE: 63

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Pro Leu Val Val Phe Gly Gly Gly Thr Lys Leu Thr Val Leu
            100                 105                 110

Gly Gln Pro
```

<210> SEQ ID NO 64
<211> LENGTH: 113
<212> TYPE: PRT
<213> ORGANISM: Artificial Sequence
<220> FEATURE:
<223> OTHER INFORMATION: U4-5-VL

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Thr Trp Asp Ser Leu
                85                  90                  95

Arg Gly Trp Val Phe Gly Gly Gly Thr Lys Leu Thr Val Leu Gly Gln
                100                 105                 110

Pro

<210> SEQ ID NO 65
<211> LENGTH: 115
<212> TYPE: PRT
<213> ORGANISM: Artificial Sequence
<220> FEATURE:
<223> OTHER INFORMATION: U4-8-VL

<400> SEQUENCE: 65

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Tyr Trp Val Phe Gly Gly Gly Thr Lys Leu Thr Val Leu
                100                 105                 110

Gly Gln Pro
        115

<210> SEQ ID NO 66
<211> LENGTH: 113
<212> TYPE: PRT
<213> ORGANISM: Artificial Sequence
<220> FEATURE:
<223> OTHER INFORMATION: U4-6-VL

<400> SEQUENCE: 66

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Leu Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gln
            100                 105                 110

Pro
```

<210> SEQ ID NO 67
<211> LENGTH: 115
<212> TYPE: PRT
<213> ORGANISM: Artificial Sequence
<220> FEATURE:
<223> OTHER INFORMATION: U4-7-VL and U4-9-VL

<400> SEQUENCE: 67

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Arg Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Asn Val Val Phe Gly Gly Gly Thr Lys Leu Thr Val Leu
            100                 105                 110

Gly Gln Pro
        115
```

<210> SEQ ID NO 68
<211> LENGTH: 13
<212> TYPE: PRT
<213> ORGANISM: Artificial Sequence
<220> FEATURE:
<223> OTHER INFORMATION: U4-7 and U4-9 CDRL1

<400> SEQUENCE: 68

```
Ser Gly Ser Ser Ser Asn Ile Gly Ser Asn Thr Val His
1               5                   10
```

HUMAN ANTI-FGFR4 ANTIBODY

This application is being filed as the national stage patent application of PCT International Patent Application No. PCT/EP2015/068440, filed on 11 Aug. 2015, and claiming priority to European Patent Application Serial No. 14180555.6, filed on 11 Aug. 2014, and entitled "HUMAN ANTI-FGFR4 ANTIBODY," the contents of both of which is incorporated herein by reference in its entirety.

The present invention relates to novel antibodies against the FGF receptor 4 (FGFR4) and to the medical use thereof, in particular for the diagnosis prevention or treatment of diseases associated with FGFR expression, overexpression or hyperactivity.

Fibroblast growth factors (FGFs) are a family of growth factors with diverse biological activities with members involved in angiogenesis, wound healing, embryonic development and various endocrine signaling pathways. The human FGF family comprises 18 members, which are structurally related signaling molecules. They exert their biological activity by interacting with their cognate receptors (FGFRs), a family of receptor tyrosine kinases. The mammalian FGFR family has four members: FGFR1-4, each consisting of three extracellular immunoglobulin-type domains (D1-D3), a single-span transmembrane domain and an intracellular split tyrosine kinase domain. FGFs interact mostly with the D2 and D3 domains. Each FGFR binds to a specific subset of the FGFs. Most FGFs can bind to several different FGFR subtypes whereas others activate specifically one receptor or one isoform of a receptor.

The receptor-ligand interactions result in receptor dimerization and autophosphorylation, formation of complexes with membrane-associated and cytosolic accessory proteins, and initiation of multiple signaling cascades. The FGFR-FGF signaling system plays important roles in the development and tissue repair by regulating cellular functions and processes such as growth, differentiation, migration, morphogenesis and angiogenesis.

FGFR4 signaling is activated by several FGFs that activate also other members of the FGFR family (Ornitz et al., 1996, *J. Biol. Chem.*, 1996, 271: 15292-7) while FGF19 is specific for FGFR4 (Xie et aL, 1999, *Cytokine*, 11(10):720-35). The activation of the FGFR4 receptor results in several types of cell signaling including the setting-up of a phosphorylation cascade-mediated signaling pathway subsequent to stimulation of FGFR4 by FGF. Upon binding of the ligand to the extracellular domain of FGFR4, receptor dimerization and subsequent phosphorylation of tyrosine kinase residues results in activation of signaling pathways by inducing the binding of signaling molecules to the receptor (Vainikka et al., 1992, *EMBO*, 11(12):4273-4280, and 1994, *J. Biol. Chem.* 269:18320-18326). For example, FGFR4 associates with PLCγ1, and an increase in MAP kinase activation and DNA synthesis upon a FGF simulation has been observed. Further interaction with other human FGF growth factor receptor family members may expand the signaling potential of FGFR4 and is a means not only for signal diversification but also signal amplification (McKeehan W. L. and Kan M., 1994, *Mol. Reprod. Dev.* 39:69-82). An 85 kDa serine kinase has been found to negatively regulate tyrosine phosphorylation of FGFR4, but its exact function has not been elucidated (Vainikka et al., 1996, *J. Biol. Chem.* 271:1270-1273). Association of FGFR4 with NCAM has been demonstrated to mediate integrin-dependent adhesion (Cavallaro et al., 2001, *Nat. Cell Biol.* 3:650-657), which might play a decisive role in tumor metastasis.

FGFR4 has been reported to have several cellular roles. The receptor is involved in the control of various cell differentiation processes in vitro and in vivo such as skeleton muscle differentiation and regeneration, mesenchymal differentiation, or osteogenesis or else in the formation of alveoli during postnatal hepatic development. Further, FGFR4 is described in the control of bile acid and cholesterol homeostasis and is thought to be involved in the control of adiposity. Furthermore, the balance between bile production and cholesterol production is controlled by FGFR4 in vitro and in vivo. FGFR4 is also involved in certain tumor phenomena such as the development of hepatocellular carcinomas or colon cancers, or in the proliferation of mammary fibroadenoma cells or of mammary cancer epithelial cells such as mammary or colorectal carcinoma cell motility. The overexpression of FGFR4 is also described in certain pancreatic cancer lines and correlates with astrocytoma malignancy.

The involvement of FGFR4 in various disorders makes the receptor an interesting target for diagnostic and therapeutic applications. In this context, an effective strategy is the usage of antibodies against FGFR4. In particular, antibodies that interfere with FGFR4-mediated signaling are desirable. Examples of anti-FGFR4 antibodies are described in the literature such as in international applications WO 03/063893, WO 2012/138975, WO 2013/0183319 and in US application US 2011/0150903. Bumbaca et al. (mAbs 3:4, 1-11; 2011) describes a humanized anti-FGFR4 antibody that binds with high specificity to FGF receptor 4. This antibody is used herein as a comparative example and referred to as GT-13. However, there continues to be a need for new anti-FGFR4 antibodies.

The problem underlying the present invention was to provide novel anti-FGFR4 antibodies and methods for using same in diagnosing, preventing and/or treating diseases associated with FGFR4 expression, overexpression and/or hyperactivity.

In particular, there was a need for new human antibodies against FGFR4. A problem usually occurring with recombinant produced antibodies is that the protein sequences of antibodies produced in a non-human immune system are partially distinct from homologous antibodies occurring naturally in humans. They are therefore potentially immunogenic when administered to human patients. Thus, it was found that monoclonal antibodies designed for human administration should preferably be modified to increase their similarity to antibody variants produced naturally in humans. Especially advantageous are those antibodies being completely human, i.e. which do not contain any parts being of non-human origin. Therefore, the present invention aims at providing human anti-FGFR4 antibodies which are advantageous for the diagnostic and therapeutic usage with humans. The desired antibodies should preferably prevent FGFR4 signaling. The invention as described herein meets this demand and provides further benefits.

A first aspect of the invention is a human antibody which is directed against an epitope between amino acids 119-248, preferably amino acids 152-240 (Ig like domain 2), more preferably between amino acids 230 and 240 of human FGFR4 or a functional fragment or functional derivative of said antibody.

The antibody is suitable for use in medicine, particularly human medicine, more particularly for the diagnosis, prevention and/or treatment of diseases associated with FGFR4 expression, overexpression and/or hyperactivity.

The invention also provides conjugates including an antibody as herein described. In particular, antibody drug conjugates are a subject-matter of the invention.

Another aspect of the invention is a fusion protein, wherein an antibody of the invention is linked to IL-2 or a functional fragment thereof.

A further aspect of the invention is a nucleic acid molecule encoding the antibody, optionally in operative linkage to an expression control sequence.

A further aspect of the invention is a host, in particular a recombinant cell which comprises the nucleic acid molecule. The cell may be used for the preparation of the antibody.

Still a further aspect of the invention is a pharmaceutical composition comprising the antibody, the nucleic acid molecule or the host, optionally together with a pharmaceutically acceptable carrier.

Still a further aspect of the invention is a method for the diagnosis, prevention and/or treatment of a disease associated with FGFR4 expression, overexpression and/or hyperactivity.

The present invention refers to a human antibody directed against FGFR4 or a functional fragment or functional derivative thereof. The term "antibody" particularly refers to molecules comprising at least one immunoglobulin heavy chain and at least one immunoglobulin light chain. Each heavy and light chain may comprise a variable and a constant domain. The antigen binding site may be formed from the variable domains of a heavy and light chain. A variable region (also referred to as variable domain) comprises complementarity determining regions (CDRs), e.g. a CDR1, a CDR2 and a CDR3 region and framework regions (FRs) flanking the CDRs. The term "complementarity determining region" is readily understood by the skilled person (see for example Harlow and Lane (eds.), *Antibodies: A Laboratory Manual*, CSHL press, Cold Spring Harbor, N.Y., 1988) and refers to the stretches of amino acids within the variable domain of an antibody that primarily make contact with the antigen and determined antibody specificity. This region is also known as the hypervariable region.

The term "human antibody" encompasses fully human or humanized antibodies, wherein fully human antibodies are preferred. Human antibodies may be prepared from genetically engineered animals, e.g. animals comprising a xenogenic immune system or from antibody display libraries according to known techniques. Human antibodies are described generally in van Dijk and van de Winkel (*Curr. Opin. Pharmacol.* 5: 368-74 (2001)) and Lonberg (*Curr. Opin. Immunol.* 20: 450-459 (2008)). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see for example Lonberg, *Nat. Biotech.* 23: 1117-1125 (2005). Human variable regions from intact antibodies generated by such animals may be further modified, e.g. by combining with a different human constant region.

Human antibodies can also be made by hybridoma-based methods. Human myeloma and mouse-human heteromyeloma cell lines for the production of human monoclonal antibodies have been described (see e.g. Kozbor *J. Immunol.* 133: 3001 (1984); Brodeur et al., *Monoclonal Antibody Production Techniques and Applications*, pp. 51-63). Human antibodies generated via human B-cell hybridoma technology are also described in Li et al, *Proc. Natl. Acad. Sci., USA* 103: 3557-3562 (2006).

Human antibodies may also be generated by phage display methods (see e.g., U.S. Pat. No. 6,248,516, 5,403,484, 5,969,108, 5,885,793, 6,696,248, 5,849,500). Techniques for selecting human antibodies from antibody libraries are known in the art. (see e.g., Carmen, S. et al., Briefings in Functional Genomics and Proteomics (2002), 1 (2), p. 189-203; and Siriwardena, D. et al., Ophthalmology (2002) 109 (3), p. 427-431). For example, a phage display method can be used, which involves causing human antibody variable regions to be expressed as a single-chain antibody (scFv) on phage surface and selecting phages binding to antigens (Nature (1991), 352, (6336), p. 624-628, Journal of Molecular Biology (1992), 227, (2), p 381-388, and Nature Biotechnology (2005), 23, (9), p. 1105-1116). Likewise, another phage display method can also be used, which involves causing human antibody Fab (antigen-binding fragment) to be expressed on the surface of phage and selecting phages binding to antigens (WO 97/08320 and WO 01/05950). Genes of the phages selected based on antigen binding can be analyzed to thereby determine DNA sequences encoding human antibody variable regions binding to the antigens. When the DNA sequence of scFv or Fab binding to the antigens is clarified, CDR sequences are extracted therefrom, and expression vectors having the sequences can be prepared and introduced into appropriate hosts, followed by gene expression to obtain human antibodies (WO 92/01047, WO 92/20791, WO 93/06213, WO 93/11236, WO 93/19172, WO 95/01438, WO 95/15388, Annu. Rev. Immunol (1994) 12, p. 433-455, and Nature Biotechnology (2005) 23 (9), p. 1105-1116).

Human antibodies may also be generated by isolating Fv clone variable domain sequences selected from human-derived phage display libraries. Such variable domain sequences may then be combined with a desired human constant domain. Techniques for selecting human antibodies from antibody libraries are known in the art.

Humanized antibodies may be prepared by humanization of monoclonal antibodies according to known techniques. Typically, a non-human antibody is humanized to reduce immunogenicity to humans, while retaining the specificity and affinity of the parental non-human antibody. Humanized antibodies and methods of making them are reviewed, e.g. in *Alamagro and Fransson, Front. Biosci.* 13: 1619-1633 (2008).

The invention also encompasses fragments of human antibodies, e.g. portions of the above-mentioned antibodies which comprise at least one antigen binding site. Examples of antibody fragments include Fab fragments, Fab' fragments, F(ab')$_2$ fragments, Fv fragments, diabodies or single chain antibody molecules and other fragments as long as they exhibit the desired capability of binding to human FGFR4. For a review of certain antibody fragments see Hudson et al., *Nat. Met.* 9: 129-134 (2003).

Diabodies are antibody fragments with two antigen binding sites that may be bivalent or bispecific. See for example Hudson et aL, (2003). Single-chain antibodies are antibody fragments comprising all or a portion of the heavy chain variable domain or all, or a portion of the light chain variable domain of an antibody. Antibody fragments can be made by various techniques including but not limited to proteolytic digestion of an intact antibody as well as production by recombinant hosts (e.g. *E. coli* or phage) as described herein.

In certain embodiments, an antibody provided herein is a multispecific antibody, e.g. a bispecific antibody. Multispecific antibodies are monoclonal antibodies that have binding specificities for at least two different sites.

In certain embodiments, one of the binding specificities is for FGFR4 and the other is for any other antigen.

In certain embodiments, bispecific antibodies may bind to two different epitopes of FGFR4. Bispecific antibodies may also be used to localize cytotoxic agents to cells which express FGFR4. Bispecific antibodies can be prepared as full-length antibodies or antibody fragments.

Techniques for making multispecific antibodies include but are not limited to recombinant co-expression of two immunoglobulin heavy chain-light chain pairs having different specificities and "knob in hole" engineering. Multispecific antibodies may also be made by engineering electrostatic steering effects for making antibody Fc-heterodimeric molecules; crosslinking two or more antibodies or fragments; using leucine zippers to produce bispecific antibodies; using "diabody" technology for making bispecific antibodies and using single-chain Fv and preparing trispecific antibodies as described. Engineered antibodies with three or more functional antigen binding sites including "octopus antibodies" are also included herein.

In certain embodiments, amino acid sequence variants of the antibodies provided herein are contemplated as long as they exhibit the desired capability of binding to human FGFR4. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from and/or insertions into and/or substitutions of residues within the amino acid sequences of the antibody. Any combination of deletion, insertion and substitution can be made to arrive at the final construct, provided that the final construct possesses the desired characteristics, e.g. antigen binding.

The term "bind" or "binding" of an antibody means an at least temporary interaction or association with or to a target antigen, i.e. human FGFR4 comprising fragments thereof containing an epitope.

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. $10^{-9}$ M to $10^{13}$ M).

In one embodiment, Kd is measured by a radio-labeled antigen binding assay (Radioimmunoassay, RIA) performed with the Fab version of an antibody of interest and its antigen.

According to another embodiment, Kd is measured using surface plasmon resonance assays with immobilized antigen. According to a preferred embodiment of the present invention, the antibodies are human monoclonal antibodies directed against an epitope of human FGFR4 as described herein.

The inventors of the present application found that antibodies directed against an epitope between amino acids 119-284 of human FGFR4 (SEQ ID NO: 70) or functional fragments or functional derivatives thereof are particularly useful for therapeutic and diagnostic applications. Particularly preferred are human antibodies directed against an epitope between amino acids 152-240 and more preferably between amino acids 230 and 240 of human FGFR4.

According to a particularly preferred embodiment, the antibody of the invention is directed against an epitope comprising, essentially consisting of or consisting of the amino acid sequence RYNY (SEQ ID NO: 69).

The epitope recognized by a human antibody of the invention is preferably located in the Ig-like domain 2 of human FGFR4.

The antibodies of the invention may be of various immunoglobulin (Ig) types, for example of the IgA-, IgD-, IgE-, IgG- or IgM-type, preferably of the IgG- or IgM-type including but not limited to the IgG1-, IgG2-, IgG3-, IgG4-, IgM1 and IgM2-type. In one preferred embodiment the antibody is of the IgG1type.

In certain embodiments of the present invention, the antibody may comprise specific heavy chain complementarity determining regions CDRH1, CDRH2 and/or CDRH3 as described herein below.

In one embodiment, the human antibody comprises a heavy chain complementarity determining region 1 (CDRH1) having the amino acid sequence as shown in any one of SEQ ID NOs: 1-6, or an amino acid sequence differing in 1 or 2 amino acids therefrom.

In a further embodiment, the antibody comprises a heavy chain complementarity determining region 2 (CDRH2) having the amino acid sequence as shown in any one of SEQ ID NOs: 7-12, or an amino acid sequence differing in 1 or 2 amino acids therefrom.

In yet a further embodiment, the antibody comprises a heavy chain complementarity determining region 3 (CDRH3) having the amino acid sequence as shown in any one of SEQ ID NOs: 13-20, or an amino acid sequence differing in 1 or 2 amino acids therefrom.

The antibody according to the invention may also comprise specific light chain complementarity determining regions CDRL1, CDRL2 and/or CDRL3.

Accordingly, in one embodiment, the antibody comprises a light chain complementarity determining region 1 (CDRL1) having the amino acid sequence as shown in any one of SEQ ID NOs: 21-23 and 68, or an amino acid sequence differing in 1 or 2 amino acids therefrom.

In a further embodiment, the antibody comprises a light chain complementarity determining region 2 (CDRL2) having the amino acid sequence as shown in any one of SEQ ID NOs: 24-27, or an amino acid sequence differing in 1 or 2 amino acids therefrom.

In yet a further embodiment, the antibody comprises a light chain complementarity determining region 3 (CDRL3) having the amino acid sequence as shown in any one of SEQ ID NOs: 28-35, or an amino acid sequence differing in 1 or 2 amino acids therefrom.

The antibody of the present invention may preferably comprise a specific combination of CDRs (i.e. of CDRH1, CDRH2 and CDRH3) within one heavy chain.

Accordingly, in one preferred embodiment, the antibody comprises a heavy chain comprising complementarity determining regions CDRH1, CDRH2 and CDRH3, wherein CDRH1 is selected from the sequences as shown in SEQ ID NOs: 1-6, or an amino acid sequence differing in 1 or 2 amino acids therefrom, CDRH2 is selected from the sequences shown in SEQ ID NOs: 7-12, or an amino acid sequence differing in 1 or 2 amino acids therefrom, and CDRH3 is selected from the sequences shown in SEQ ID NOs: 13-20, or an amino acid sequence differing in 1 or 2 amino acids therefrom.

Most preferably, the antibody of the invention comprises a heavy chain comprising three CDRs, wherein the combination of CDRH1, CDRH2 and CDRH3 is selected from those shown in table 1. It is understood that each line of this table represents one specific combination of a CDRH1, a CDRH2 and a CDRH3.

TABLE 1

| CDRH1 | CDRH2 | CDRH3 |
|---|---|---|
| RNYMS (SEQ ID NO. 1) | AISGSGGSTYYADSVKG (SEQ ID NO. 7) | VTSPGAFDI (SEQ ID NO. 13) |
| KAWMS (SEQ ID NO. 2) | AISGSGGSTYYADSVKG (SEQ ID NO. 7) | LYSYGDFDH (SEQ ID NO. 14) |
| DYYMS (SEQ ID NO. 3) | TISGSGGSTYYADSVKG (SEQ ID NO. 8) | LTAYGHVDS (SEQ ID NO. 15) |
| SNYMS (SEQ ID NO. 4) | LISGSGGSTYYADSVQG (SEQ ID NO. 9) | NTAGFGYFDL (SEQ ID NO. 16) |
| SNYMN (SEQ ID NO. 5) | VISYDGSNKYYADSVKG (SEQ ID NO. 10) | KSRDFWRGPFDY (SEQ ID NO. 17) |
| SNYMS (SEQ ID NO. 4) | SISGSGGRTYYADSVKG (SEQ ID NO. 11) | MTVFGAATL (SEQ ID NO. 18) |
| DYYMN (SEQ ID NO. 6) | AIGGSGDRTYYADSVKG (SEQ ID NO. 12) | GGSYFGY (SEQ ID NO. 19) |
| DYYMS (SEQ ID NO. 3) | AISGSGGSTYYADSVKG (SEQ ID NO. 7) | LATYGPFDD (SEQ ID NO. 20) |

According to the present invention, it is further preferred that the antibody comprises a specific combination of CDRs within one light chain (i.e. of CDRL1, CDRL2 and CDRL3).

Thus, in one preferred embodiment, the antibody comprises a light chain comprising complementarity determining regions CDRL1, CDRL2 and CDRL3, wherein CDRL1 has the amino acid sequence as shown in any of SEQ ID NOs: 21-23 and 68, or an amino acid sequence differing in 1 or 2 amino acids therefrom, CDRL2 has the amino acid sequence as shown in any of SEQ ID NOs: 24-27, or an amino acid sequence differing in 1 or 2 amino acids therefrom, and CDRL3 has the amino acid sequence as shown in any of SEQ ID NOs: 28-35, or an amino acid sequence differing in 1 or 2 amino acids therefrom.

Most preferably, the antibody of the invention comprises a light chain comprising three CDRs, wherein the combination of CDRL1, CDRL2 and CDRL3 is selected from those shown in table 2. It is understood that each line of this table represents one specific combination of a CDRL1, a CDRL2 and a CDRL3.

TABLE 2

| CDRL1 | CDRL2 | CDRL3 |
|---|---|---|
| SGGTSNIGTNTVN (SEQ ID NO, 21) | RNNQRPS (SEQ ID NO. 24) | AAWDDSLNGPYVV (SEQ ID NO. 28) |
| SGSSSNIGSNTVN (SEQ ID NO. 22) | RNNQRPS (SEQ ID NO. 24) | AAWDDSLNGPAVV (SEQ ID NO. 29) |
| SGSSSNIGTNTVN (SEQ ID NO. 23) | RNYQRPS (SEQ ID NO. 25) | AAWDDSLSGPHVV (SEQ ID NO. 30) |
| SGSSSNIGSNTVN (SEQ ID NO. 22) | RNNQRPS (SEQ ID NO. 24) | AAWDDSLNGPLVV (SEQ ID NO. 31) |
| SGSSSNIGSNTVN (SEQ ID NO. 22) | RNNQRPS (SEQ ID NO. 24) | STWDDSLRGWV (SEQ ID NO. 32) |
| SGSSSNIGSNTVN (SEQ ID NO. 22) | RNNQRPS (SEQ ID NO. 24) | AAWDDSLNGPYWV (SEQ ID NO. 33) |
| SGSSSNIGSNTVN (SEQ ID NO. 22) | YDDLLPS (SEQ ID NO. 26) | AAWDDSLNGPV (SEQ ID NO. 34) |
| SGSSSNIGSNTVH (SEQ ID NO. 68) | RNNRRPS (SEQ ID NO. 27) | AAWDDSLSGPNVV (SEQ ID NO. 35) |

As described above, the complementarity determining regions (CDRs) of an antibody may be flanked by framework regions. A heavy or light chain of an antibody containing three CDRs contains e.g. four framework regions.

Additionally, the present invention also encompasses those antibodies that recognize the same epitope on human FGFR4 as a specific antibody characterized by the above heavy and/or light chain CDRs. Functional fragments and functional derivatives of those antibodies are also within the scope of the invention. To determine the epitope on FGFR4 recognized by the antibody, chemically prepared arrays of protein sequence derived short peptides derived from the amino acid sequence of the extracellular domain of human FGFR4 can be used to locate and identify antibody epitopes (Reinicke W., *Methods Mol. Biol.* 2004, 248: 443-63). A further method to map the epitopes in the FGFR4 extracellular domain bound by the antibodies of the invention comprises Snaps/SELDI (Wang et al., *Int. J. Cancer,* 2001, Jun. 15; 92 (6): 871-6) or a routine cross-blocking assay such as described in Antibodies, A Laboratory Manual, Cold Spring Harbor Laboratory, Ed Harlow and David Lane (1988) can be performed.

According to a particularly preferred embodiment, the human antibody of the invention comprises a heavy chain comprising at least one CDR selected from the group consisting of
(a) a CDRH1 as shown in SEQ ID NO: 1-6, or a CDRH1 sequence differing in 1 or 2 amino acids therefrom,
(b) a CDRH2 as shown in SEQ ID NO: 7-12, or a CDRH2 sequence differing in 1 or 2 amino acids therefrom, and
(c) a CDRH3 as shown in SEQ ID NO: 13-20, or a CDRH3 sequence differing in 1 or 2 amino acids therefrom,
and/or a light chain comprising at least one CDR selected from the group consisting of
(d) a CDRL1 as shown in SEQ ID NO: 21-23 or 68, or a CDRL1 sequence differing in 1 or 2 amino acids therefrom,
(e) a CDRL2 as shown in SEQ ID NO: 24-27, or a CDRL2 sequence differing in one or two amino acids therefrom, and
(f) a CDRL3 as shown in SEQ ID NO: 28-35, or a CDRL3 sequence differing in 1 or 2 amino acids therefrom.

In a preferred embodiment of the invention, the human antibody comprises a heavy chain variable region (VH) as shown in any one of SEQ ID NOs. 52-59 or a sequence differing in 1 or 2 amino acids therefrom. Furthermore, the human antibody of the invention preferably comprises a light chain variable region (VL) as shown in any one of SEQ ID NOs. 60-67 or a sequence differing in 1 or 2 amino acids therefrom. Particularly preferred are human antibodies comprising a heavy chain variable region as shown in any one of SEQ ID NOs. 52-59 and a light chain variable region as shown in in any one of SEQ ID NOs. 60-67.

Particularly preferred is a human antibody (U4-1) comprising a heavy chain comprising a CDRH1 as shown in SEQ ID NO: 1, a CDRH2 as shown in SEQ ID NO: 7 and a CDRH3 as shown in SEQ ID NO: 13 and a light chain comprising a CDRL1 as shown in SEQ ID NO: 21, a CDRL2 as shown in SEQ ID NO: 24 and a CDRL3 as shown in SEQ ID NO: 28. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 52 and a light chain variable region according to SEQ ID NO: 60. Also encompassed are human antibodies wherein the sequences of the variable region of the heavy chain and/or the light chain differ in 1 or 2 amino acids from those shown in SEQ ID NOs. 52 and 60.

Particularly preferred is a human antibody (U4-2) comprising a heavy chain comprising a CDRH1 as shown in SEQ ID NO: 2, a CDRH2 as shown in SEQ ID NO: 7 and a CDRH3 as shown in SEQ ID NO: 14 and a light chain comprising a CDRL1 as shown in SEQ ID NO: 22, a CDRL2 as shown in SEQ ID NO: 24 and a CDRL3 as shown in SEQ ID NO: 29. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 53 and a light chain variable region according to SEQ ID NO: 61. Also encompassed are human antibodies wherein the sequences of the variable region of the heavy chain and/or the light chain differ in 1 or 2 amino acids from those shown in SEQ ID NOs. 53 and 61.

Particularly preferred is a human antibody (U4-3) comprising a heavy chain comprising a CDRH1 as shown in SEQ ID NO: 3, a CDRH2 as shown in SEQ ID NO: 8 and a CDRH3 as shown in SEQ ID NO: 15 and a light chain comprising a CDRL1 as shown in SEQ ID NO: 23, a CDRL2 as shown in SEQ ID NO: 25 and a CDRL3 as shown in SEQ ID NO: 30. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 54 and a light chain variable region according to SEQ ID NO: 62. Also encompassed are human antibodies wherein the sequences of the variable region of the heavy chain and/or the light chain differ in 1 or 2 amino acids from those shown in SEQ ID NOs. 54 and 62.

Particularly preferred is a human antibody (U4-4) comprising a heavy chain comprising a CDRH1 as shown in SEQ ID NO: 4, a CDRH2 as shown in SEQ ID NO: 9 and a CDRH3 as shown in SEQ ID NO: 16 and a light chain comprising a CDRL1 as shown in SEQ ID NO: 22, a CDRL2 as shown in SEQ ID NO: 24 and a CDRL3 as shown in SEQ ID NO: 31. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 55 and a light chain variable region according to SEQ ID NO: 63. Also encompassed are human antibodies wherein the sequences of the variable region of the heavy chain and/or the light chain differ in 1 or 2 amino acids from those shown in SEQ ID NOs. 55 and 63.

Particularly preferred is a human antibody (U4-5) comprising a heavy chain comprising a CDRH1 as shown in SEQ ID NO: 5, a CDRH2 as shown in SEQ ID NO: 10 and a CDRH3 as shown in SEQ ID NO: 17 and a light chain comprising a CDRL1 as shown in SEQ ID NO: 22, a CDRL2 as shown in SEQ ID NO: 24 and a CDRL3 as shown in SEQ ID NO: 32.

Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 56 and a light chain variable region according to SEQ ID NO: 64. Also encompassed are human antibodies wherein the sequences of the variable region of the heavy chain and/or the light chain differ in 1 or 2 amino acids from those shown in SEQ ID NOs. 56 and 64.

Particularly preferred is a human antibody (U4-6) comprising a heavy chain comprising a CDRH1 as shown in SEQ ID NO:6, a CDRH2 as shown in SEQ ID NO: 12 and a CDRH3 as shown in SEQ ID NO: 19 and a light chain comprising a CDRL1 as shown in SEQ ID NO: 22, a CDRL2 as shown in SEQ ID NO: 26 and a CDRL3 as shown in SEQ ID NO: 34. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 58 and a light chain variable region according to SEQ ID NO: 66. Also encompassed are human antibodies wherein the sequences of the variable region of the heavy chain and/or the light chain differ in 1 or 2 amino acids from those shown in SEQ ID NOs. 58 and 66.

Particularly preferred is a human antibody (U4-7) comprising a heavy chain comprising a CDRH1 as shown in SEQ ID NO: 3, a CDRH2 as shown in SEQ ID NO: 7 and a CDRH3 as shown in SEQ ID NO: 20 and a light chain comprising a CDRL1 as shown in SEQ ID NO: 68, a CDRL2 as shown in SEQ ID NO: 27 and a CDRL3 as shown in SEQ ID NO: 35. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 59 and a light chain variable region according to SEQ ID NO: 67. Also encompassed are human antibodies wherein the sequences of the variable region of the heavy chain and/or the light chain differ in 1 or 2 amino acids from those shown in SEQ ID NOs. 59 and 67.

Particularly preferred is a human antibody (U4-8) comprising a heavy chain comprising a CDRH1 as shown in SEQ ID NO: 4, a CDRH2 as shown in SEQ ID NO: 11 and a CDRH3 as shown in SEQ ID NO: 18 and a light chain comprising a CDRL1 as shown in SEQ ID NO: 22, a CDRL2 as shown in SEQ ID NO: 24 and a CDRL3 as shown in SEQ ID NO: 33. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 57 and a light chain variable region according to SEQ ID NO: 65. Also encompassed are human antibodies wherein the sequences of the variable region of the heavy chain and/or the light chain differ in 1 or 2 amino acids from those shown in SEQ ID NOs. 57 and 65.

Also preferred is a human antibody (U4-9) comprising a heavy chain comprising a CDR1 as shown in SEQ ID NO: 3, a CDRH2 as shown in SEQ ID NO: 8 and a CDRH3 as shown in SEQ ID NO: 15 and a light chain comprising a CDRL1 as shown in SEQ ID NO: 68, a CDRL2 as shown in SEQ ID NO: 27 and a CDRL3 as shown in SEQ ID NO: 35. Also encompassed are human antibodies, wherein one or more of the CDRs differ in one or two amino acids or antibodies recognizing the same epitope on human FGFR4.

In a particularly preferred embodiment the human antibody comprises a heavy chain variable region according to SEQ ID NO: 54 and a light chain variable region according to SEQ ID NO: 67. The antibody U4-9 preferably comprises the heavy chain as specified for antibody U4-3 and the light chain as specified for antibody U4-7. In the experiments provided in the present application the antibody U4-9 proved to have a higher affinity for FGFR4 than U4-3.

As mentioned above, the antibodies of the invention show advantageous properties with respect to their binding specificity and biological activity, in particular with respect to their capability to recognize epitopes of the human anti-FGFR4, to decrease cell growth and cell migration, their ability to activate a further antineoplastic agent and/or sensitize tumor cells to a therapeutic treatment. The antibodies of the invention U4-1 to U4-9 have intrinsic antitumor activity. They specifically bind to FGFR4 and preferably show no cross-reactivity to other FGF receptors FGFR1-3b, c.

The antibodies are capable of inhibiting ligand binding to human FGFR4. The effect of the antibody on ligand binding to FGFR4 can be determined by incubating cells which express this receptor (e.g. MDA-MB453 breast cancer cells) with radiolabelled ligand in the absence (control) or presence of the anti-FGFR4 antibody. Those antibodies which reduce the binding affinity of ligand for the FGFR4 receptor or which block binding of ligand to FGFR4 can be identified. Known FGFR4 ligands include FGF1, FGF2, FGF4, FGF6, FGF8, FGF9, FGF17, FGF18, FGF19 and FGF20. A cell line which endogenously expresses FGF19 is Huh-7. The antibodies of the invention are capable of at least partially inhibiting binding of these ligands to human FGFR4. Particularly preferred antibodies of the present invention are capable of blocking binding of one or more of the above ligands by at least 60%, preferably at least 70% and more preferably at least 80% or 87%. Particularly preferred are those antibodies of the invention, which block binding of FGF19 to human FGFR4 by at least 80%, more preferably at least 85% or at least 90%.

Blocking of ligand binding to human FGFR4 results in inhibition of FGFR4 signaling. To select for antibodies which reduce ligand-induced FGFR4 phosphorylation, cells can be pre-incubated with buffer (control) or antibody, then treated with ligand or a control buffer. The cells are then lysed and the crude lysates can be centrifuged to remove insoluble material. Supernatants may be incubated with the antibody-specific pure FGFR4 and protein-A-sepharose to enable efficient precipitation. Following washing, the immunoprecipitates may be separated by SDS-PAGE. Western blots of the gels are then probed with anti-phosphotyrosine antibody. After visualization, the blots may be stripped and reprobed with an anti-FGFR4 antibody. Reflectance scanning densitometry of the gel can be performed in order to quantify the effect of the antibody in question on HRG-induced formation of the complex. Those antibodies which reduce FGFR4 phosphorylation relative to control (untreated cells) are selected.

In vitro experiments can be conducted in order to determine the ability of the antibodies of the invention to inhibit ligand-stimulated cell proliferation. An appropriate number of cells of interest are incubated with antibodies diluted in appropriate medium. Cells are stimulated by adding ligand directly to antibody solution and are then left to grow for 72 h. Alamar Blue™ (Thermo Fisher Scientific, Waltham, Mass.; U.S.A.) is added and incubated at 37° C. in the dark. Absorbance is measured at 590 nm every 30 min.

To select for those antibodies which reduce FGFR4-mediated cell migration, transmigration experiments can be performed. Serum-starved cells are incubated with antibody. An appropriate number of cells may be placed in the top chamber of coated transwell plates with 8 µm pores (BD Biosciences, San Jose, Calif.; U.S.A.). In the case of stimulation medium alone or containing a chemotactic agent is used in the bottom chamber. Cells are left to migrate and are subsequently stained. Stained nuclei are counted; percent inhibition is expressed as inhibition relative to a control antibody.

It was found that the antibodies of the invention have an improved anti-tumor activity as compared to known anti-FGFR4 antibodies. The anti-tumor efficacy of therapeutic antibodies may be evaluated in human xenograft tumor studies. In these studies, human tumors grow as xenografts in immunocompromised mice and therapeutic efficacy is measured by the degree of tumor growth inhibition (TGI). In order to determine if the FGFR4 antibodies of the invention interfere with tumor growth of human cancer cells in nude mice, cells are implanted in nude mice. Tumors are subcutaneously grown on the back or in the flanks of the animal. Treatment may be started immediately or when tumors reach a certain mean volume. Prior to the first treatment, mice are randomized and statistical tests are performed to assure uniformity in starting tumor volumes (mean, median and standard deviation) across treatment groups. Treatment is started with a loading dose of 25 mg/kg followed by 25 mg/kg injections twice a week by intraperitoneal injection.

The antibody of the present invention is suitable for use in medicine, particularly for use in human medicine. The antibody may be used in the prevention and/or treatment of diseases associated with FGFR4 expression, overexpression and/or hyperactivity. Examples for diseases that can be prevented and/or treated using an antibody of the invention are detailed below.

Furthermore, the antibody of the invention may be used as a diagnostic agent, for example for the diagnosis of diseases associated with FGFR 4 expression, overexpression and/or hyperactivity. Examples of diseases that can be diagnosed using an antibody of the invention are described herein below.

The antibody of the present invention may be coupled to a heterologous group, e.g. an effector group. Such an antibody conjugate is especially suitable for therapeutic applications. The term "effector group" may refer to a cytotoxic group, such as a radioisotope or a radionuclide, a toxin, a therapeutic group or another effector group known in the art. Conjugates wherein the antibody is coupled to a therapeutic group, so-called antibody-drug-conjugates (ADCs) are particularly preferred. Alternatively, the antibody of the invention may be coupled to a labeling group. Such an antibody conjugate is particularly suitable for diagnostic applications. As used herein, the term "labeling group" refers to a detectable marker, e.g. a radiolabeled amino acid or biotin moiety, a fluorescent marker, an enzyme or any other type of marker which is known in the art. The linking of antibodies or antibody fragments of the invention to radioisotopes e.g. provides advantages to tumor treatments. Unlike chemotherapy and other forms of cancer treatment, radioimmunotherapy or the administration of a radioisotope-antibody combination targets the cancer cells with minimal damage to surrounding normal healthy tissue.

A further embodiment of the present invention is a fusion protein wherein an antibody as defined above is fused to interleukin-2 (IL-2). Interleukin-2 is a 15 kDa cytokine produced by T helper cells that stimulates cytotoxic T lymphocytes and NK cells. IL-2 has been used clinically in the treatment of melanoma and renal cell carcinoma to stimulate cancer patient's immune systems. Achieving a prolonged high dose of IL-2 in the tumor can result in the induction of a long-lasting anti-tumor response leading to the rejection of an otherwise lethal tumor. In the present invention it has been demonstrated that it is possible to incorporate IL-2 into a fusion protein including an antibody of the invention while maintaining its activity. Hence, a fusion protein wherein an antibody of the invention is fused to IL-2 is suitable to serve as a delivery system which retains antigen binding specificity and possesses the full activity of IL-2.

The invention also refers to a nucleic acid molecule encoding the antibody as described above. The term "nucleic acid molecule" encompasses DNA, e.g. single- or double-stranded DNA or RNA. The DNA may be of genomic, cDNA or synthetic origin, or a combination thereof. The nucleic acid molecule of the invention may be in operative linkage to an expression control sequence, i.e. to a sequence which is necessary to effect the expression of coding nucleic acid sequences. Such expression control sequences may include promoters, enhancers, ribosomal binding sites and/or transcription termination sequences. Specific examples of suitable expression control sequences are known in the art.

According to a preferred embodiment, the invention is directed to an isolated nucleic acid molecule selected from the group consisting of
  (a) a nucleic acid sequence encoding an antibody, a fragment or a derivative thereof as defined above,
  (b) a nucleic acid sequence as shown in any one of SEQ ID NOs: 36-43 and SEQ ID NOs. 44-51,
  (c) a nucleic acid sequence complementary to any one of the sequences in (a) or (b), and
  (d) a nucleic acid sequence capable of hybridizing to (a), (b) or (c) under stringent conditions.

According to a particularly preferred embodiment of the invention, a nucleic acid molecule comprises a sequence encoding the variable region of the heavy chain and a sequence encoding the variable region of the light chain of the antibody. In an alternative embodiment, a combination of two nucleic acid molecules is provided, wherein one nucleic acid molecule encodes the light chain of the antibody and the other nucleic acid molecule encodes the heavy chain of the antibody. The nucleic acid sequence encoding the variable region of the heavy chain is preferably selected from the sequences as shown in any one of SEQ ID NOs. 36-43. The nucleic acid sequence encoding the variable region of the light chain of the antibody is preferably selected from the sequences as shown in any one of SEQ ID NOs. 44-51. Particularly preferred is a combination of nucleic acid sequences comprising at least one of the sequences as shown in SEQ ID NOs. 36-43 and at least one of the sequences shown in SEQ ID NOs. 44-51. The nucleic acid sequences may be present within one isolated nucleic acid molecule or in a combination of two isolated nucleic acid molecules.

The term "hybridizing under stringent conditions" means that two nucleic acid fragments hybridize with one another under standardized hybridization conditions as described, for example in Sambrook et al., "*Expression of cloned Genes in E. coli*" in *Molecular Cloning: A Laboratory Manual* (1989), Cold Spring Harbor Laboratory Press, New York, USA. Such conditions are, for example, hybridization in 6.0×SSC (Saline Sodium Citrate) at about 45° C. followed by a washing step with 2.0×SSC at 50° C., preferably 2.0×SSC at 65° C. or 0.2×SSC at 50° C., preferably 0.2×SSC at 65° C.

The nucleic acid molecule of the invention may be located on a vector which may additionally contain a replication origin and/or a selection marker gene. Examples of vectors are e.g. plasmids, cosmids, phages, viruses etc. Thus, a further embodiment of the invention is a vector comprising a nucleic acid sequence as disclosed herein. Preferably, the vector is an expression vector. Said vector may, for example, be a phage, plasmid, viral or retro viral vector. Retro viral vectors may be replication competent or replication defective. In the latter case, viral propagation generally will occur only in complementing hosts/cells.

The nucleic acid molecules of the invention may be joined to a vector containing selectable markers for propagation in a host. Generally, a plasmid vector is introduced in a precipitate such as a calcium phosphate precipitate or rubidium chloride precipitate or in a complex with a charged lipid or in carbon-based clusters such as fullerenes. Should the vector be a virus, it may be packed in vitro using an appropriate packaging cell line prior to application to host cells.

Preferably, the vector of the invention is an expression vector, wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well-known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g. the lac, trp or tac promoter in *E. coli*, and examples for regulatory elements permitting expression in eukaryotic host cells are the AOXI or GAL-1 promoter in yeast or the CMV (Cytomegalovirus)-, SV40 (Simian Virus 40)-, RSV-promoter (Rous sarcoma virus), CMV-enhancer, SV40-enhancer or a globin intron in mammalian and other animal cells. Beside elements which are responsible for the initiation of transcription, such regulatory elements may also comprise transcription termination signals such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 or pSPORTI (Thermo Fisher Scientific). Preferably, said vector is an expression vector and/or a gene transfer or targeting vector. Expression vectors derived from viruses such as retrovirus, vaccina virus, adeno-associated virus, herpes virus or bovine papilloma virus may be used for delivery of the polynucleotides or vector of the invention into targeted cell population. Methods which are well-known to those skilled in the art can be used to construct recombinant viral vectors; see for example the techniques described in Sambrook, *Molecular Cloning, A Laboratory Manual*, Cold Spring Harbor Laboratory Press (2001, 3$^{rd}$ edition), N.Y and Ausubel, *Current Protocols in Molecular Biology*, Green Publishing Associates and Wiley Interscience, N.Y. (1994). Alternatively, the nucleic acid molecules of the invention can be reconstituted into liposomes for delivery to target cells.

Further, the invention refers to a host which comprises the nucleic acid molecule or the vector as described above. The nucleic acid molecule or the vector may be introduced into the host by transformation, transfection or transduction according to any method known in the art.

Said host may be a prokaryotic or eukaryotic cell or a non-human transgenic animal. The polynucleotide or vector of the invention which is present in the host may either be integrated into the genome of the host or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, *Proc. Natl. Acad. Sci. USA*, 87 (1990), 4712-4716; Joyner, *Gene Targeting, A Practical Approach*, Oxford University Press.

The host can be any prokaryotic or eukaryotic cell such as a bacterial, insect, fungal, plant, animal, mammalian or preferably a human cell. Preferred fungal cells are, for example those of the genus Saccharomyces, in particular those of the species *S. cerevisiae*. The term "prokaryotic" is meant to include all bacteria which can be transformed or transfected with a polynucleotide for the expression of a variant polypeptide of the invention. Prokaryotic hosts may include gram negative as well as gram positive bacteria such as for example *E. coli, Salmonella typhimurium, Serratia marcescens* and *Bacillus subtilis*. A polynucleotide coding for a mutant form of variant polypeptides of the invention can be used to transform or transfect the host using any of the techniques commonly known to those of ordinary skill in the art. Methods for preparing fused operably linked genes and expression them in bacteria or animal cells are well-known in the art (Sambrook, *Molecular Cloning, A Laboratory Manual*, Cold Spring Harbor Laboratory Press (2001, $3^{rd}$ edition). The genetic constructs and methods described therein can be utilized for expression of variant antibodies, antibody fragments or derivatives thereof of the invention in e.g. prokaryotic hosts. In general, expression vectors containing promoter sequences, which facilitate the efficient transcription of the inserted nucleic acid molecule, are used in connection with the host. The expression vector typically contains an origin of replication, a promoter and a terminator as well as specific genes which are capable of providing phenotypic selection of the transformed cells. The transformed prokaryotic hosts can be grown in fermentors and cultured according to techniques known in the art to achieve optimal cell growth. The antibodies, antibody fragments or derivatives thereof of the invention can then be isolated from the growth medium, cellular lysates or cellular membrane fractions. The isolation and purification of the microbially or otherwise expressed antibodies, antibody fragments or derivatives thereof of the invention may be by any conventional means, such as for example preparative chromatographic separations and immunological separations such as those involving the use of monoclonal or polyclonal antibodies.

According to one embodiment of the invention, the host is a human, bacteria, animal, fungal, amphibian or plant cell. Preferred animal cells include but are not limited to Chinese hamster ovary (CHO) cells, baby hamster kidney (BHK) cells, monkey kidney cells (COS), mouse embryonic fibroblast cells (NIH-3T3) and a number of other cell lines, including human cells.

In another preferred embodiment, said animal cell is an insect cell. Preferred insect cells include but are not limited to cells from the SF9 cell lines.

Preferably, the cell is a mammalian cell, e.g. a hamster, rabbit or human cell. Most preferably, the cell is a human cell. Said human cells include but are not limited to human embryonic kidney cells (HEK293, 293T, 293 freestyle). Furthermore, said human cell lines include but are not limited to HeLa cells, human hepatocellular carcinoma cells (e.g. HEPG2, Huh-7), A549 cells. According to another embodiment, the host of the present invention is a nonhuman transgenic animal. The invention provides transgenic non-human animals comprising one or more nucleic acid molecules of the invention that may be used to produce antibodies of the invention. Antibodies can be produced in and recovered from tissue or body fluids, such as milk, blood or urine of goats, cows, horses, pigs, rats, mice, rabbits, hamsters or other mammals. See for example U.S. Pat. No. 5,827,690; 5,756,687; 5,750,172; and 5,741,957. As described above, non-human transgenic animals that comprise human immunoglobulin loci can be produced by immunizing with FGFR4 or a portion thereof.

The antibody of the invention may be prepared by a method, wherein said antibody is obtained from a host as described herein above. Thus, a further embodiment of the present invention is a method for the preparation of an antibody comprising culturing the host of the invention under conditions that allow synthesis of said antibody and recovering said antibody from said culture.

The transformed hosts can be grown in fermentors and cultured according to techniques known in the art to achieve optimal cell growth. Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like; see Scopes, *"Protein Purification"*, Springer-Verlag, N.Y. (1982). The antibody or its corresponding immunoglobulin chain(s) of the invention can then be isolated from the growth medium, cellular lysates or cellular membrane fractions. The isolation and purification of the e.g. microbially expressed antibodies or immunoglobulin chains of the invention may be by any conventional means, such as for example preparative chromatographic separations and immunological separations such as those involving the use of monoclonal or polyclonal antibodies directed e.g. against the constant region of the antibody of the invention.

It will be apparent to those skilled in the art that the antibodies of the invention can be further coupled to other moieties, e.g. drug targeting and imaging applications. Such coupling may be conducted chemically after expression of the antibody or antigen to side of attachment or the coupling product may be engineered into the antibody or antigen of the invention at the DNA level. The DNAs are then expressed in a suitable host system, and the expressed proteins are collected and renatured if necessary.

According to one embodiment, a recombinant cell as described above is cultured under conditions which allow expression of the antibody encoding nucleic acid molecules. The antibody may be collected from the cultured cell or the culture supernatant. Preferably, the antibody is prepared from a mammalian, particularly from a human cell.

Still a further aspect of the present invention relates to a pharmaceutical composition comprising the antibody, the conjugate, the fusion protein, the nucleic acid molecule, the vector or the host as described above, optionally together with a pharmaceutically acceptable carrier.

The term "carrier" includes agents, e.g. diluents, stabilizers, adjuvants or other types of excipients that are non-toxic to the cell or mammal to be exposed thereto at the dosages and concentrations employed. Examples of pharmaceutically acceptable carriers are well-known in the art and include phosphate-buffered saline solutions, water, emulsions such as oil/water emulsions, various types of wetting agents, sterile solutions, etc. Often, the pharmaceutically acceptable carrier is an aqueous pH-buffered solution which is useful for drug delivery, particularly for the delivery of antibody molecules. The pharmaceutical composition may be formulated by wellknown conventional methods, i.e. by mixing the active agent with carriers and optionally other agents that are usually incorporated into the formulation. For example, the composition may be formulated in the form of lyophilized formulations, aqueous solutions, dispersions or solid preparations.

Administration of the suitable compositions may be effected by different ways, e.g. by intravenous, intraperitoneal, subcutaneous, intramuscular, topical, intradermal, intranasal or intrabronchial administration. The compositions of the invention may also be administered directly to the target site, e.g. by biolistic delivery to an external or internal target site, like the brain. The dosage regimen will be determined by the attending physician and clinical factors.

The present invention also encompasses the administration of the pharmaceutical composition to a subject in need thereof, particularly a human patient suffering from a disorder associated with FGFR4 expression, overexpression and/or hyperactivity. As is well-known in the medical arts, dosages for any one patient depend upon many factors including the patient's size, body surface and area, age, the particular compound to be administered, sex, time and route of administration, general health and other drugs being administered concurrently. Depending on the type and severity of the condition to be treated, about 1 µg/kg to 15 mg/kg of the active ingredient may be administered to a patient in need thereof, e.g. by one or more separate administrations or by continuous infusion. A typical daily dosage might range from about 1 µg/kg to about 100 mg/kg, depending on the factors mentioned above. For repeated administrations over several days or longer, depending on the condition to be treated, the treatment is sustained until a desired suppression of the disease or the symptoms occurs. The composition may be administered by any suitable route, for example by parental, subcutaneous, intranasal, intravascular, intravenous, intraarterial or intrathecal injection or infusion.

Progress can be monitored by periodic assessment. The compositions of the inventions may be administered locally or systemically. Preparations for parental administration include sterile aqueous or non-aqueous solutions, suspensions and emulsions. Examples of non-aqueous solvents are propylenes, glycol, polyethylene glycol, vegetable oils such as olive oil, and injectable organic esters such as ethyl-oleate. Aqueous carriers include water, alcoholic/aqueous solutions, emulsions or suspensions, including saline and buffered media. Parental vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present, such as for example antimicrobials, antioxidants, chelating agents and inert gases, and the like.

The active agent according to the present invention may be administered together with other active agents. The additional active agent(s) may be administered separately or as a part of the pharmaceutical composition of the present invention.

According to a preferred embodiment of the invention, the pharmaceutical composition of the invention may comprise further agents depending on the intended use of the pharmaceutical composition. It is particularly preferred that the pharmaceutical composition comprises further active agents like e.g. an additional antineoplastic agent, small-molecule inhibitor, anti-tumor agent or chemotherapeutic agent. The invention also relates to a pharmaceutical composition comprising the antibody of the invention in combination with at least one further antineoplastic agent. Such combination is effective for example in inhibiting abnormal cell growth.

Many antineoplastic agents are presently known in the art. In one embodiment, the antineoplastic agent is selected from the group of therapeutic proteins including but not limited to antibodies or immunomodulatory proteins.

In another embodiment, the antineoplastic agent is selected from the group of small-molecule inhibitors or chemotherapeutic agents consisting of mitotic inhibitors, kinase inhibitors, alkylating agents, antimetabolites, intercalating antibodies, growth factor inhibitors, cell cycle inhibitors, enzymes, topoisomerase inhibitors, histone deacetylase inhibitors, anti-survival agents, biological response modifiers, anti-hormones, e.g. anti-androgens and antiangiogenesis agents.

The above-mentioned additional active agents can, of course, not only be administered together with the antibody of the invention within a mutual pharmaceutical composition, but they can also be administered separately.

In yet another embodiment, the present invention relates to a diagnostic method comprising determining the amount and/or localization of FGFR4 in the patient tissue or in a patient sample. In this embodiment, it is particularly preferred to use an antibody carrying a labeling group as described above. A comparison of the result obtained for the patient tissue or patient sample to reference data allows for the diagnosis of diseases associated with FGFR4 expression, overexpression and/or hyperactivity. The diagnostic method of the invention is useful for detecting an undesired expression, overexpression or hyperactivity of human FGFR4 in different cells, tissues or other suitable samples. Accordingly, the onset or the disease state of diseases associated with FGFR4 expression, overexpression and/or hyperactivity can be assessed. The diagnostic method of the invention may also include a step of establishing a treatment regimen for the patient on the basis of the obtained results.

In another embodiment, the present invention relates to a method of assessing for the presence of FGFR4 expressing cells comprising contacting the antibody of the invention with cells or tissue suspected of carrying FGFR4 on their/its surface. Suitable methods for detecting FGFR4 expression in a sample may be an enzyme-linked immunosorbent assay (ELISA) or immunohistochemistry (IHC).

An ELISA assay may be carried out in a microtiter plate format, wherein e.g. wells of a microtiter plate are adsorbed with an anti-FGFR4 antibody. The wells are rinsed and treated with a blocking agent such as milk protein or albumin to prevent non-specific adsorption of the analyte. Subsequently, the wells are treated with a test sample. After rinsing away the test sample or standard, the wells are treated with a second anti-FGFR4 antibody that is labeled, e.g. by conjugation with biotin. After washing away excess secondary antibody, the label is detected, e.g. with avidin-conjugated horseradish peroxidase (HRP) and a suitable chromogenic substrate. A concentration of the FGFR4 antigen in the test sample is determined by comparison with a standard curve developed from standard samples.

For IHC, paraffin-embedded tissues may be used, wherein the tissues are e.g. first deparaffinized in xylene and then dehydrated e.g. with ethanol and rinsed in distilled water. Antigenic epitopes masked by formalin fixation and paraffin embedding may be exposed by epitope unmasking, enzymatic digestion or saponin. For epitope unmasking, paraffin sections may be heated in a steamer, water bath or microwave oven for 20-40 minutes in an epitope-retrieval solution as for example 2 N HCL solution (pH 1.0). In the case of enzyme digestion, tissue sections may be incubated at 37° C. for 1030 minutes in different enzyme solutions such as proteinase K, trypsin, pronase, pepsin, etc.

After rinsing away the epitope-retrieval solution or excess enzyme, tissue sections are treated with a blocking buffer to prevent unspecific interactions. The primary anti-FGFR4 antibody is added at appropriate concentrations. Excess primary antibody is rinsed away and sections are incubated in peroxidase blocking solution for 10 minutes at room temperature. After another washing step, tissue sections are incubated with a secondary labeled antibody, e.g. labeled with a group that might serve as an anchor for an enzyme. Examples therefore are biotin-labeled secondary antibodies that are recognized by streptavidin-coupled horseradish peroxidase. Detection of the antibody/enzyme complex is achieved by incubating with a suitable chromogenic substrate.

In an additional embodiment, the present invention relates to a method of blocking FGFR4 function comprising contacting the antibody of the invention with cells or a tissue suspected of carrying FGFR4 on their/its surface under conditions, wherein the antibody is capable of blocking FGFR4 function. The contacting may be in vitro or in vivo.

Furthermore, the present invention relates to kits for the diagnosis or treatment of diseases associated with FGFR4 expression, overexpression and/or hyperactivity. A kit of the invention comprises at least one antibody, nucleic acid molecule and/or vector as described above. In addition, the kit may further comprise at least one other active agent or further components. A diagnostic kit of the present invention preferably comprises a labeled antibody as described herein above. Further, the diagnostic kit may comprise reference data about the amount and/or localization of FGFR4 in the same type of tissue or sample. The reference data may be obtained from one or more healthy subjects and/or from one or more subjects with a known disease state. A comparison to said reference data allows for the diagnosis of diseases associated with FGFR4 expression, overexpression and/or hyperactivity. Based on the obtained results, a treatment regimen for the patient may be established.

According to the present invention, diseases associated with FGFR4 expression, overexpression and/or hyperactivity are for example hyperproliferative diseases such as cancer. Cancer that can be diagnosed, prevented and/or treated according to the invention may be selected from the group consisting of hepatocellular carcinoma, breast cancer, gastric cancer, colon cancer, rhabdomyosarcoma, prostate cancer, ovarian cancer, soft tissue sarcoma, melanoma, head and neck squamous carcinoma and lung adenocarcinoma and other FGFR4-expressing or -overexpressing cancers and formation of tumor metastases.

According to another embodiment, the disease associated with FGFR4 expression, overexpression and/or hyperactivity is a metabolic disease, in particular metabolic syndrome or obesity.

According to a still further embodiment of the invention, the disease associated with FGFR4 expression, overexpression and/or hyperactivity is ventricular hypertrophy, heart hypertrophy or chronic kidney disease.

The present invention shall be explained in more detail by the following figures and examples.

FIGURE LEGENDS

Figure 8:
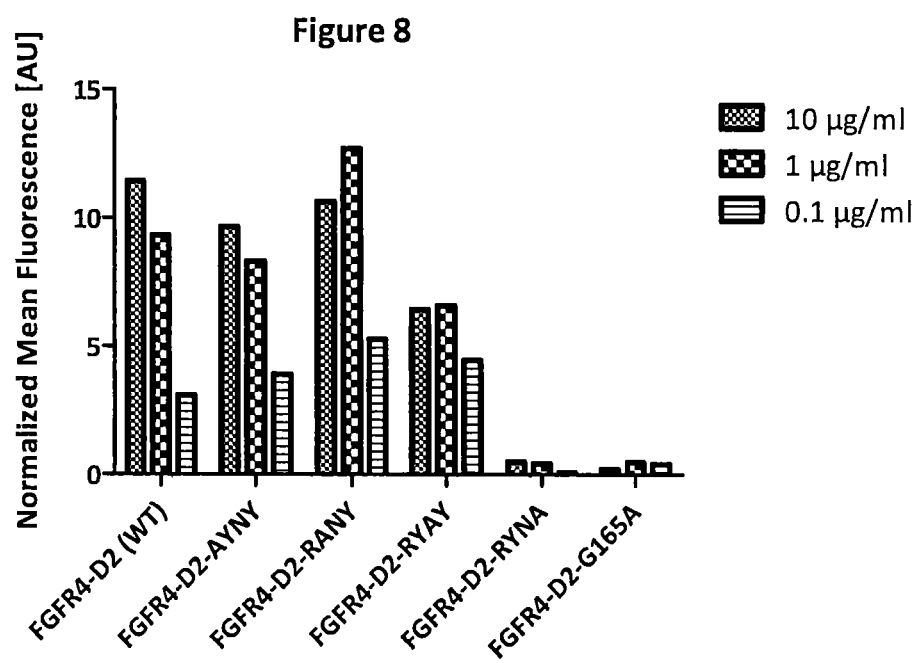

FIG. 8 is a bar graph showing the determination of the binding of antibody U4-3 to FGFR4. The results were obtained from alanine scanning mutagenesis of the FGFR4 extracellular domain. As can be seen, the binding of FGFR4 is highly specific and single acid mutagenesis in the D2 domain resulted in significantly decreased binding.

Figure 9:
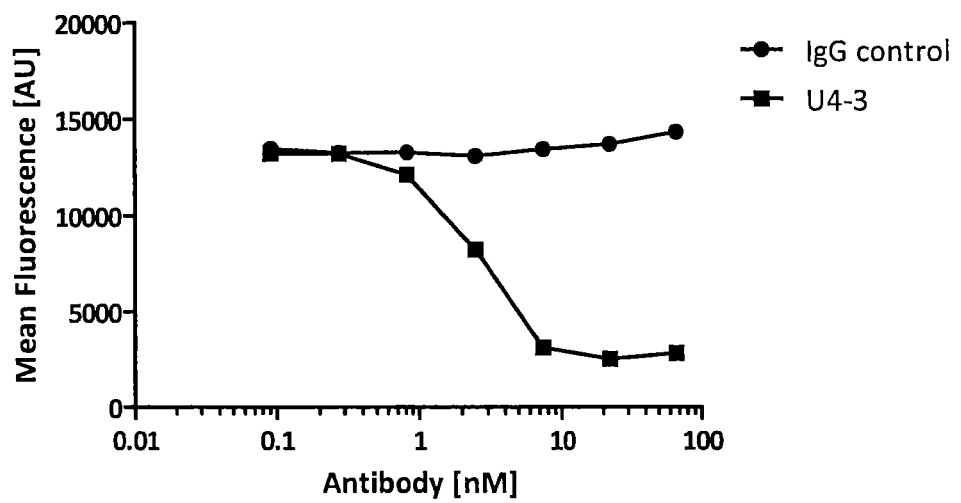

FIG. 9 is a graph showing ligand binding by anti-FGFR4 antibody U4-3. hIgG is shown as a comparative example.

Figure 10:
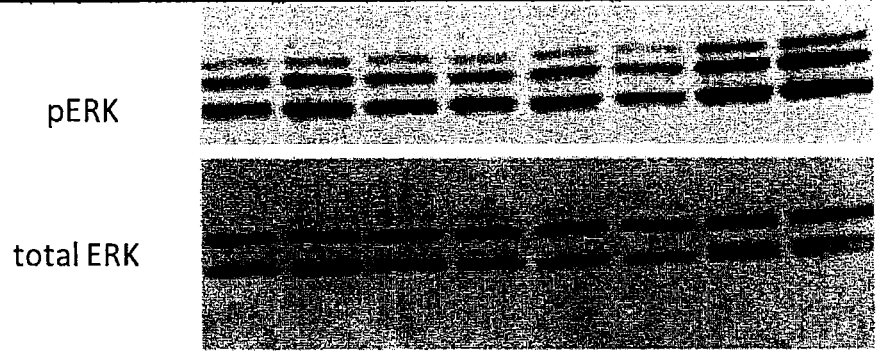
Figure 10:
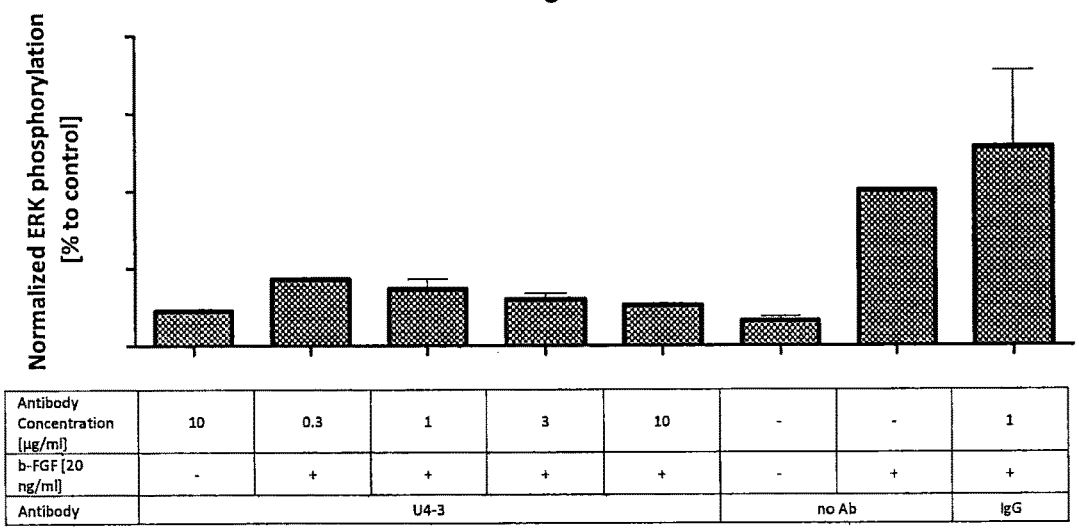

FIG. 10(A) shows a representative immunoblot for the determination of concentration-dependent inhibition of b-FGF-mediated ERK phosphorylation using different antibody concentrations of U43.

FIG. 10(B) is a bar graph showing a quantification of the data from FIG. 10(A).

Figure 12:
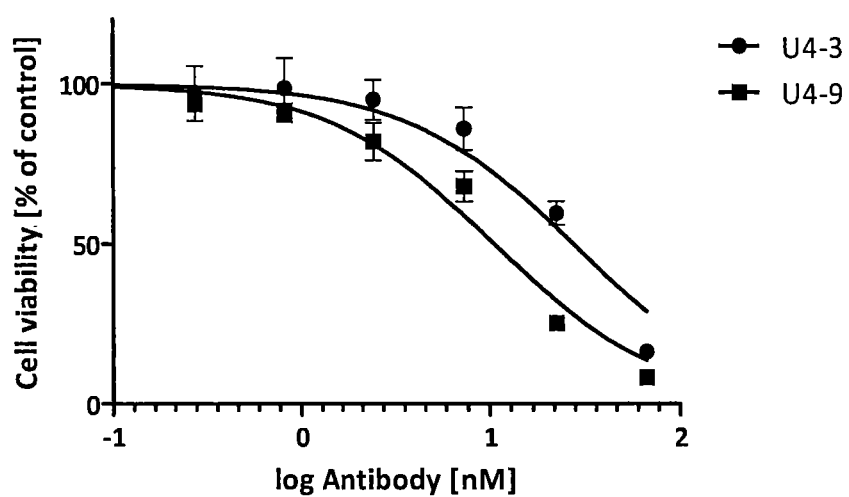

FIG. 11 shows the inhibition of endogenous FGFR4 phosphorylation by anti-FGFR4 antibody U4-3 in Huh-7 cells. A: immunoprecipitation (IP); B: total cell lysates; C: quantification of 11A FIG. 12 shows a NIH 3T3 spheroid growth assay using antibodies U43 and U4-9.

Figure 13:
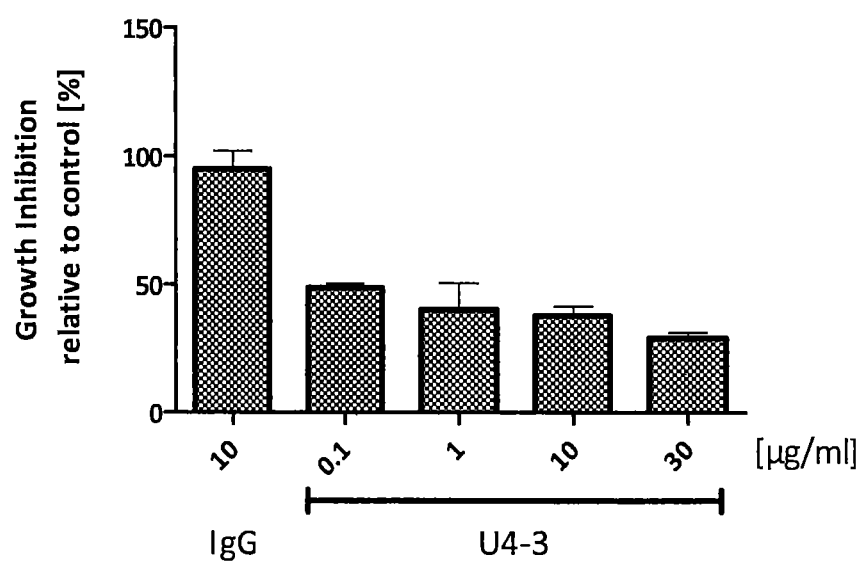

FIG. 13 is a bar graph showing the inhibition of soft agar colony growth in Huh-7 cells in the presence of anti-FGFR4 antibody U4-3 or control IgG antibody.

Figure 14:
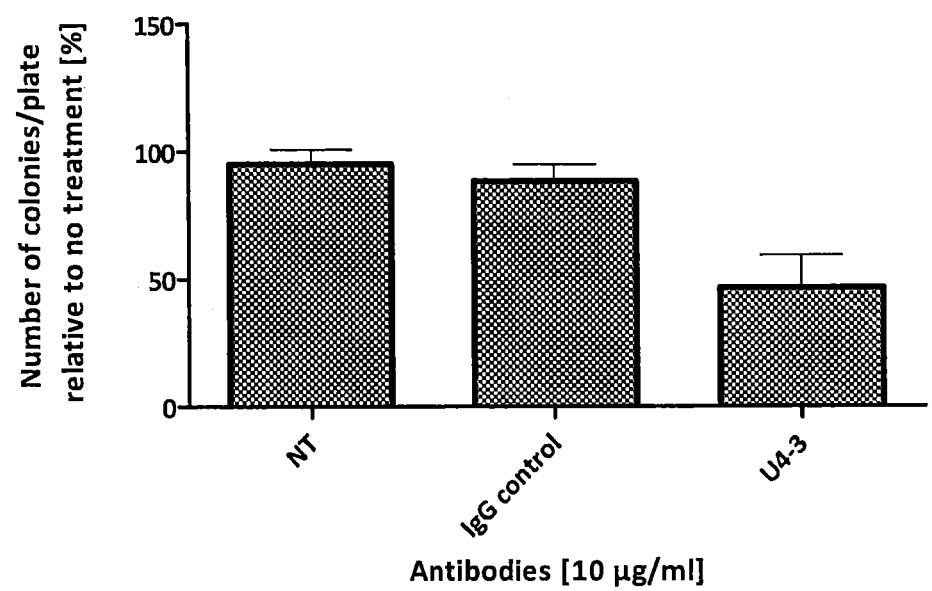

FIG. 14 is a bar graph showing the results of a cell growth assay of ZR-75-1 cells cultured in the presence of antibody U4-3 and control IgG.

Figure 15:
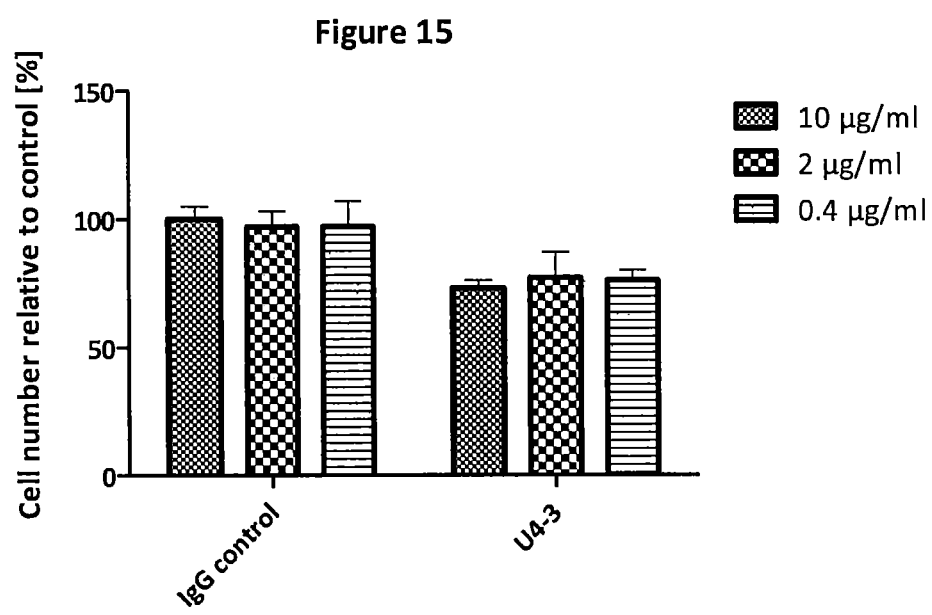

FIG. 15 is a bar graph showing the results of an MG-63 spheroid growth assay using different concentrations of U4-3 and control IgG.

Figure 16:
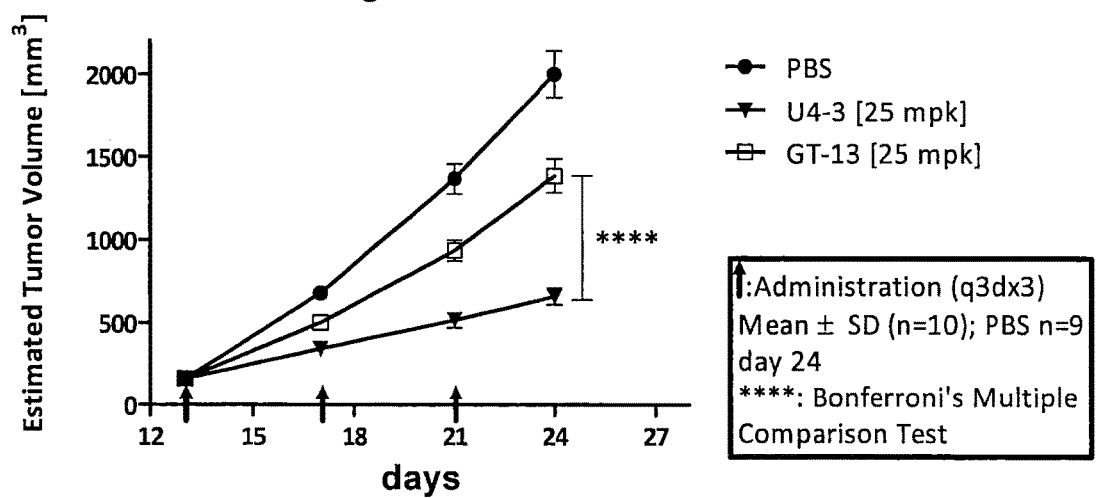

FIG. 16 is a graph showing growth inhibition mediated by anti-FGFR4 antibody U4-3 or GT-13 in a murine tumour model. A: dose-response; B: different antibodies, C: comparison to GT-13

Figure 17:
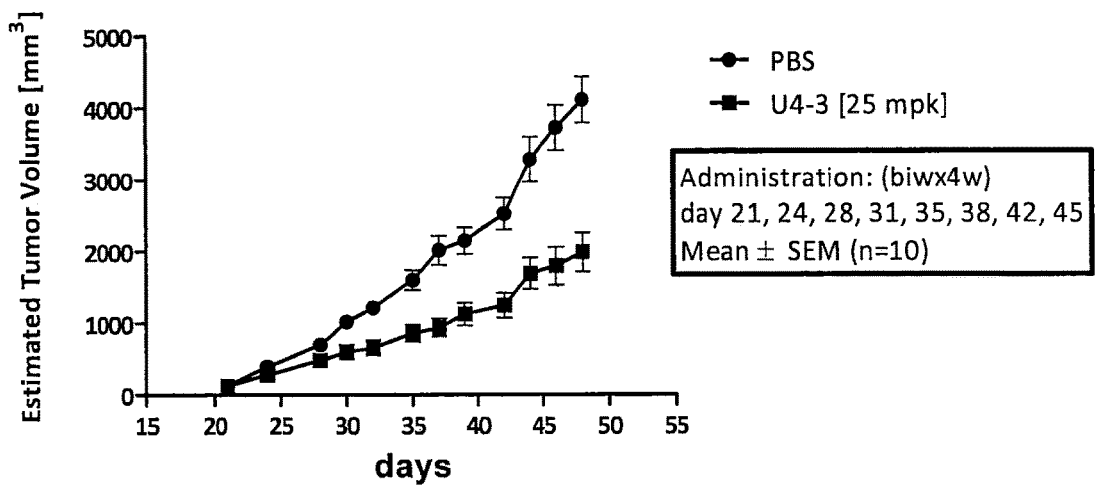
Figure 17:
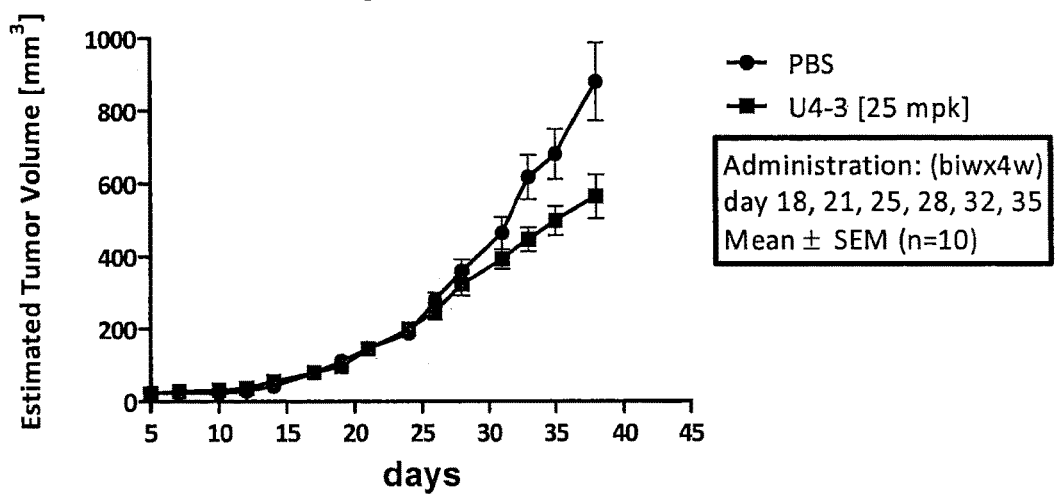

FIG. 17 in vivo growth inhibition in Huh-1 (A) and Hep3B (B) tumor models using the antibody U4-3.

Figure 18:
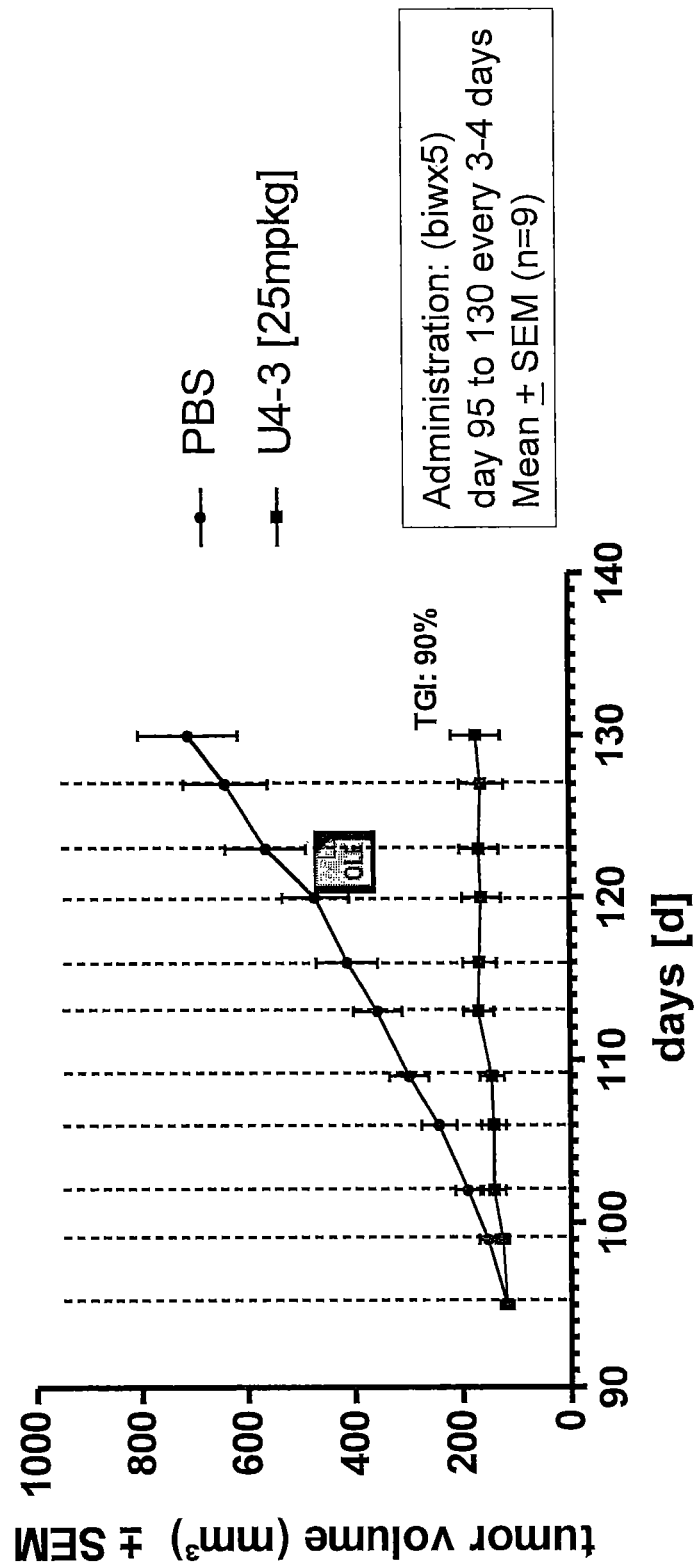

FIG. 18 in vivo growth inhibition in SNU-761 human liver xenograft models using the antibody U4-3.

Figure 19:
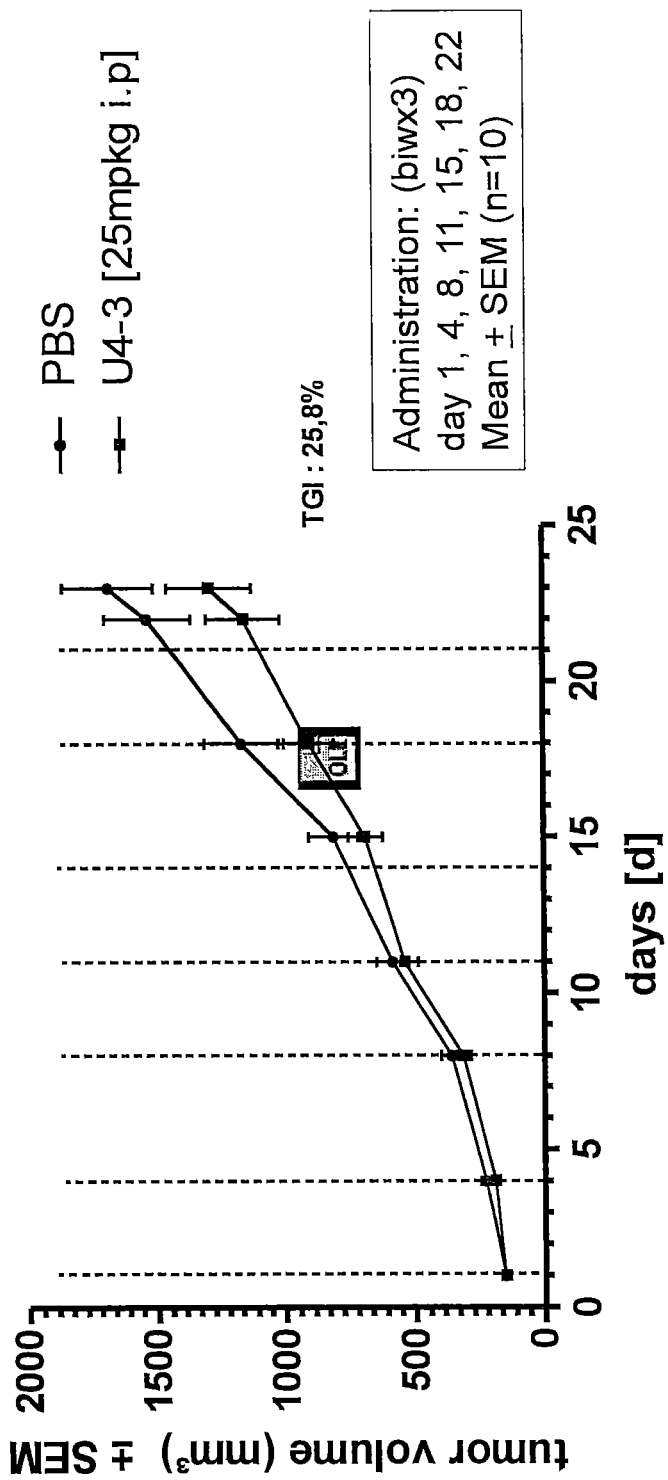

FIG. 19 in vivo efficacy in a patient-derived gastric xenograft tumor model.

Figure 20:
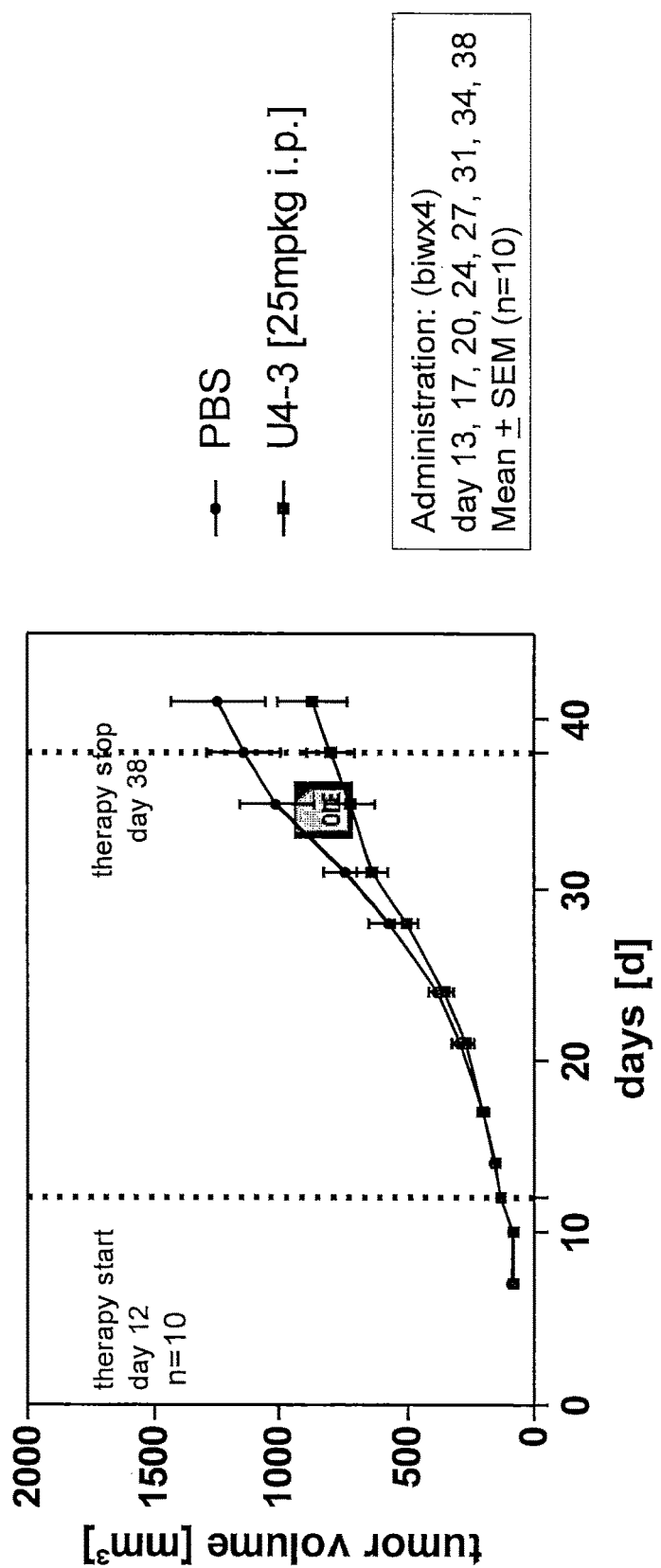

FIG. 20 in vivo efficacy in a human colon xenograft tumor model SW620.

EXAMPLES

Example 1: Generation of FGFR4 Specific Antibodies

Isolation of Fab Antibody Fragments

The n-CoDeR Fab library (BioInvent, Lund, Sweden) was used to isolate Fab antibody fragments recognizing human FGFR4. The screening was set-up as a differential panning approach either against human FGFR4-Fc (R&D Systems, Minneapolis, Minn.; U.S.A.), human FGFR4-His/Myc or the rat myoblast cell line L6 (ATCC, Manassas, Va.; U.S.A.) which stably expressed human FGFR4. Other family of human FGFRs-Fc (R&D Systems), human Fc (Jackson Immuno Research, Newmarket; UK) and L6 cell was used in the negative selection. In the liquid panning, human. FGFR4-Fc and human FGFR4-His/Myc was biotinylated with EZ-Link NHS-Chromogenic-Biotin (Thermo Fisher Scientific). Dynabeads M-280 streptavidin (Thermo Fisher Scientific) were added to retrieve FGFR4-binding phages. In the solid panning, human FGFR4-Fc and human FGFR4-His/Myc were directly immobilized on polystyrene balls. Phages were incubated with the beads, the balls or FGFR4-expressing L6 cells and unbound fractions were removed by washing. Bound phages were released by incubation with Trypsin and amplified in *E. coli*. After a total of five different pannings, *E. coli* (TOP10F') were transformed with the Fab-expression plasmids and individual Fab clones were finally expressed.

Example 2: Identification of Unique FGFR4 Binding Fabs

Fabs from the third round panning as described above were tested for binding as follows: 1 pmole of FGFR4-Fc or FGFR4-His/Myc was coated to each well of an ELISA plate and incubated overnight at 4° C. After washing and blocking the culture media of *E. coli* TOP10F' expressing the Fab was added to the wells and incubated for 1 h. Finally, the bound Fab was detected by incubating with peroxidase-conjugated anti-His-antibody (R&D Systems) or peroxidase-conjugated anti-human Fab (Jackson Immuno Research). Signal was detected by adding Super Signal ELISA Pico Chemiluminescent Substrate (Thermo Fisher Scientific). FGFR4-binding Fabs were sequenced to identify unique clones using standard sequencing techniques and purified unique Fabs were assayed for binding to L6 or 293T cells expressing human FGFR4 (transient or stable expression) by flow cytometry. Confirmed, FGFR4-binding Fab clones were converted to IgG format using standard recombinant techniques.

Example 3: Signal Neutralizing Activity by FGFR4 Binding Fabs Via Elk1 Luciferase Reporter Gene Assay Functionality of Fabs binding to FGFR4 was tested via Elk1 luciferase reporter gene assay, which was established as follows:

HEK293 cells stably expressing integrinav and integrinβ3 were seeded onto a 96-well culture plate and transiently transfected with pcDNA-DEST40-hFGFR4, pcDNA-DEST40, pFA2-Elk1 (Agilent Technologies, Santa Clara, Calif.; U.S.A.), pFR-Luc2CP, containing 5× GAL4 binding element of pFR-Luc (Agilent Technologies) placed in the cloning sites of pGAL4.12[luc2CP] and pGL4.74 [hRluc/TK] (Promega, Madison, Wis.; U.S.A.) using Lipofectamine 2000 according to the manufacturers' protocol. The next day, cells were incubated with Fabs (diluted in DMEM 2% FBS at concentrations of 10, 1, 0.1 µg/ml) for 1 h at 37° C. followed by incubation with ligand 10 ng/ml (recombinant human FGF-17 ((rhFGF17), R&D systems) for 6 h. Finally luciferase activity was determined by adding Dual-Glo Luciferase Assay System substrate (Promega). The ratio of specific (firefly luciferase) activity to signal for normalization (*renilla luciferase*) was calculated and values for the different Fabs are displayed as percentage relative to control values (Table 3). All Fabs tested showed significant inhibitory activity, reducing the signal for more than 50% at 1 µg/ml and more than 35% at 10 µg/ml.

TABLE 3

Signal neutralizing activity by FGFR4 binding Fabs via Elk1 luciferase reporter gene assay.

| FGFR4 binding Fab | Reporter assay | | |
|---|---|---|---|
| U4 Antibody | % of control (+rhFGF 17) | | |
| Clone No. | 0.1 µg/ml | 1 µg/ml | 10 µg/ml |
| U4-1 | 70.4 | 39.6 | 32.0 |
| U4-2 | 112.4 | 43.8 | 26.6 |
| U4-3 | 50.4 | 26.9 | 17.3 |
| U4-4 | 82.2 | 28.8 | 20.1 |
| U4-5 | 115.8 | 43.2 | 16.3 |
| U4-7 | 72.6 | 33.1 | 16.8 |
| U4-8 | 65.2 | 22.5 | 12.7 |

Figure 1:
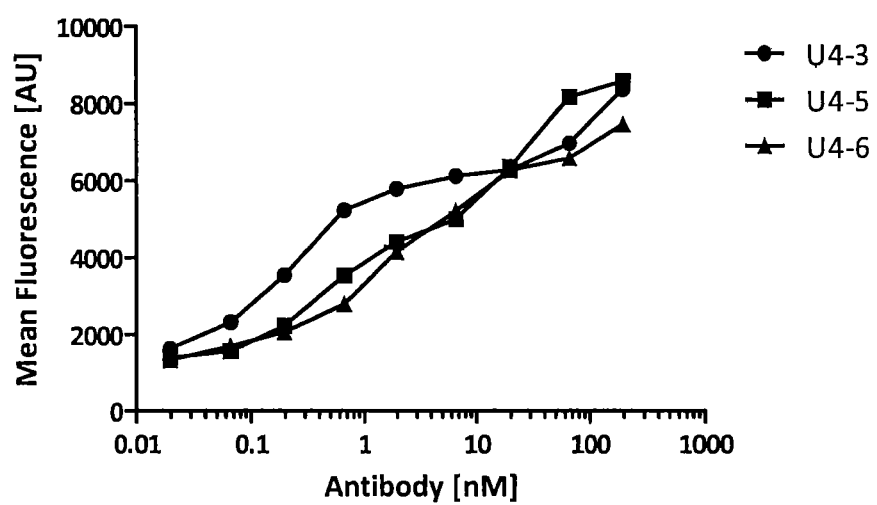
FIG. 1 shows the determination of antibody binding to Huh-7 for antibodies U4-3, U4-5 and U4-6 using a phycoerythrin-labeled anti-human IgG antibody.

Example 4: Determination of KD for Anti-FGFR4 Antibody in Huh-7 Cells by Flow Cytometry Huh-7 cells (obtained from JCRB Cell Bank) were cultured in DMEM containing 10% FBS under standard conditions at 37° C. and 5% $CO_2$. Cells were harvested with 5 mM EDTA (in PBS) and 200,000 cells per sample were incubated with indicated anti-FGFR4 antibody (1:3 serial dilution; starting concentration 30 µg/ml) for 30 min at 4° C. After incubation, cells were washed and bound antibody was determined using a Phycoerythrin-labeled anti-human IgG antibody (Jackson Immuno Research). Antibody binding to Huh-7 was measured with a BD Accuri C6 flow cytometer (BD Biosciences, San Jose, Calif.; U.S.A.) and analyzed using the AccuriC6 software. Subsequently, the equilibrium dissociation constant ($K_D$) was determined using Prism (GraphPad Software, La Jolla, Calif., U.S.A.). The calculated $K_D$ values for the U3 Pharma antibodies were very similar (between 0.2 and 1.6 nM). FIG. 1 shows a representative experiment and the $K_D$ for the remaining antibodies was determined independently. The affinity for GT-13 was found to be lower when compared to all tested U3 Pharma antibodies (Table 4).

TABLE 4

Dissociation constant ($K_D$) values for indicated antibodies against human FGFR4.

| Antibody | KD [nM] |
|---|---|
| U4-1 | 0.85 |
| U4-2 | 0.15 |
| U4-3 | 0.22 |
| U4-5 | 1.5 |
| U4-6 | 1.6 |
| U4-7 | 1.3 |
| U4-8 | 0.46 |
| GT-13 | 3.7 |

Figure 2:
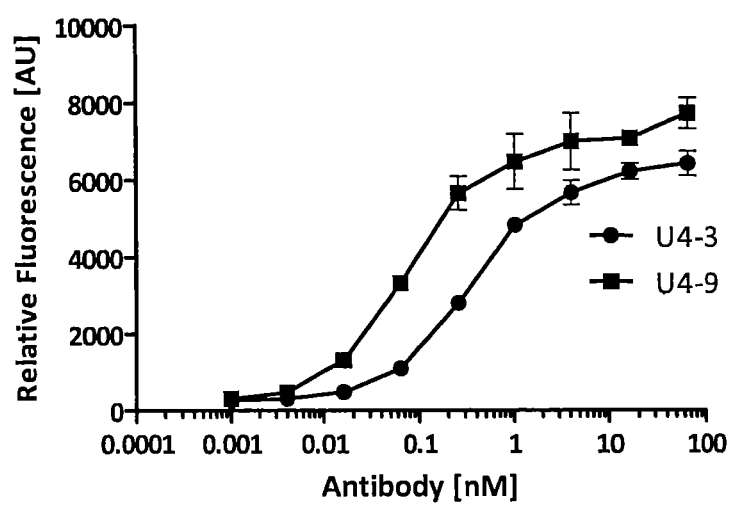
FIG. 2 shows the determination of the binding of anti-FGFR4 antibodies U43 and U4-9 to the extracellular domain of FGFR4.

Example 5: Determination of $K_D$ for Antibodies U4-3 and U4-9 Against the Extracellular Domain (ECD) of FGFR4 by ELISA Mouse anti-His tag antibody was obtained from Bio-Rad (Hercules, Calif.; U.S.A.) and coated onto MaxiSorp® flat-bottom 96 well ELISA plates (Sigma, St. Louis, Mo.; U.S.A.) at a concentration of 2 µg/ml. After coating, the extracellular domain of human FGFR4 (myc- and His-tagged) was added at a concentration of 0.01 µg/ml. After removal of unbound protein, indicated antiFGFR4 antibody was added (1:4 serial dilution, starting concentration 10 µg/ml) and binding was finally detected with the AttoPhos® AP Fluorescent Substrate System (Promega) using an alkaline-phosphatase coupled goat anti-human IgG F(ab') fragment on the Fluostar Omega fluorescent plate reader instrument from BMG Labtech (Ortenberg; Germany). A representative result is shown in FIG. 2. Subsequently, dissociation constants were calculated for U4-3, -5 and -9 using Graph Pad Prism (Table 5). All antibodies tested showed excellent KDs and the observed value for U4-3 was similar to that observed previously.

TABLE 5

Dissociation constant ($K_D$) values for U4-3 against human FGFR4 (extracellular domain).

| Antibody | KD [nM] |
|---|---|
| U4-3 | 0.34 |
| U4-5 | 0.08 |
| U4-9 | 0.07 |

Example 6: Determination of $K_D$ for U4-3 Using Biacore Assay

Standard amine coupling was applied to prepare a goat anti-human IgG capturing S-CM5 sensor chip (the reference flow cell contained the capturing antibody as well). The carboxymethylated dextran (CMD) surface was activated by injecting a mixture of 200 mM EDC and 50 mM NHS for 7 min (10 µl/min). Subsequently, 30 µg/ml anti-human IgG antibody diluted in 10 mM Na acetate pH 5.0 was injected for 7 minutes (10 µl/min). The remaining unreacted esters were quenched with 1 M Ethanolamine pH 8.5 (7 min, 10 µl/ml). Surface densities of 17892-18376 RU were obtained for the antihuman IgG antibody.

Interaction analyses of antigen with reversibly captured antibody were performed using a Biacore™ T100 instrument (GE Healthcare Bio-Sciences (Piscataway, N.J.; U.S.A.)) at 25° C. in HBS analysis buffer (10 mM HEPES pH 7.4, 150 mM NaCl, 50 µM EDTA, 0.05% Tween 20). 37-38 RU of specific antibody was captured on a flow cell. Subsequently five serial threefold dilutions of antigen (3.7, 11.1, 33.3, 100 and 300 nM) were injected in single cycle mode for 2 min, respectively (50 µl/min). The dissociation was recorded for 10 min at the same flow rate. An anti-human IgG capture antibody containing flow cell served as reference. Complete regeneration (removal of specific antibody together with bound antigen from capture surface) was accomplished by repeated injections of 10 mM glycine pH 1.7 supplemented with 5% final percentage 1,4-Dioxan.

Figure 3:
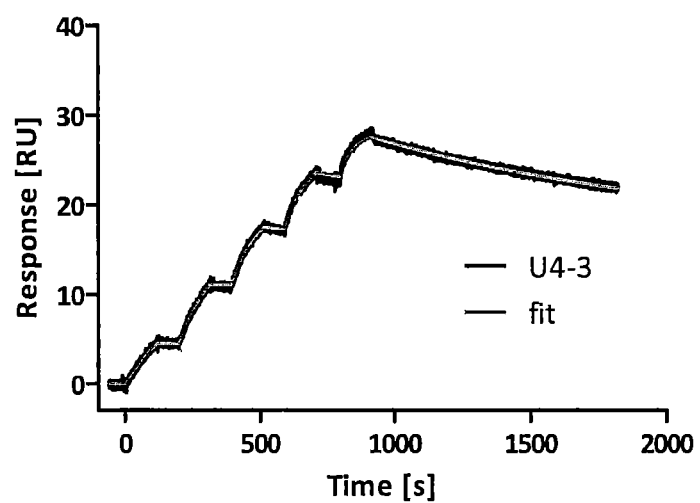
FIG. 3 shows the results of an interaction analysis of antigen with reversibly captured antibody U4-3.
Figure 4:
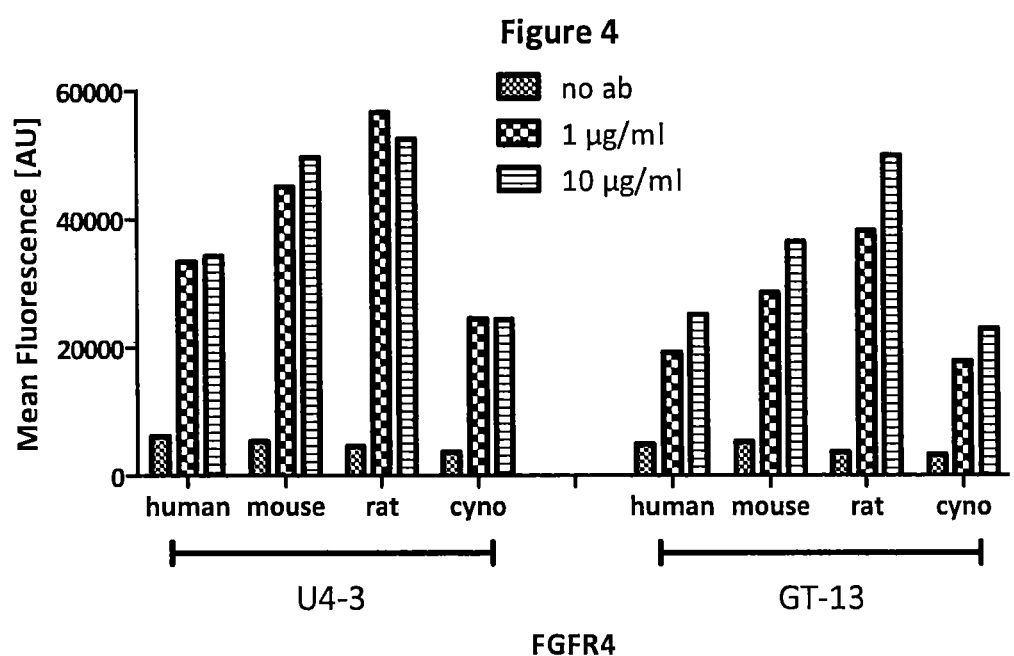
FIG. 4 shows a comparison of the species-specificity of the antibody U43 of the invention as compared to the antibody GT-13.

Data processing (e.g. blank run subtraction) and evaluation was performed by global fitting applying a bivalent analyte binding model using the Biacore T100 Evaluation Software version 2.0.3. The equilibrium dissociation constant KD1 was calculated by dividing kd1 with ka1. FIG. 3 shows a representative measurement for antibody U4-3; $K_D$ values for this antibody and U4-9 (average of 3 measurements) are reported in Table 6.

TABLE 6

Dissociation constant ($K_D$) values for indicated antibodies using Biacore assay.

| Antibody | KD [nM] |
|---|---|
| U4-3 | 0.56 |
| U4-9 | 0.12 |

Example 7: Determination of Species Specificity by Flow Cytometry

Hek293 cells were obtained from CLS (Cell Lines Service, Eppelheim; Germany) and cultured in DMEM containing 10% FBS under standard conditions at 37° C. and 5% CO2. On Day 0, cells were seeded at $4 \times 10^5$ cells/10 cm dish. After 24 h, cells were transfected with plasmids coding for FGFR4 from rat, mouse, human or cynomolgus monkey. Cells were allowed to express the proteins for 48 h and were then dissociated from the dish with 5 mM EDTA in PBS followed by incubation with indicated concentrations of anti-FGFR4 antibody U4-3 or GT-13. Binding was determined using a Phycoerythrin-conjugated anti-human IgG antibody (Jackson Immuno Research Europe). Data was acquired with a BD Accuri C6 flow cytometer (BD Biosciences.) and analyzed using the AccuriC6 software. Antibody titrations experiment (starting concentration 10 µg/ml; 1:3 dilution) allowed calculation of the dissociation constants for the antibodies (see table below). The antibody showed similar affinity to all species tested already at very low concentrations [1 µg/ml] and $K_D$ were comparable among species showing best binding against human and cynomolgus protein. U4-3, however showed better binding across all species tested when compared to GT-13.

TABLE 7

Dissociation constant ($K_D$) values for indicated antibodies against FGFR4 from different species.

| Species | KD [nM] for U4-3 | KD [nM] for GT-13 |
|---|---|---|
| Human | 0.25 | 1.462 |
| Mouse | 0.4 | 2.688 |
| Rat | 0.5 | 2.821 |
| Cynomolgus | 0.32 | 2.078 |

Example 8: Binding to Other FGFRs

Figure 5:
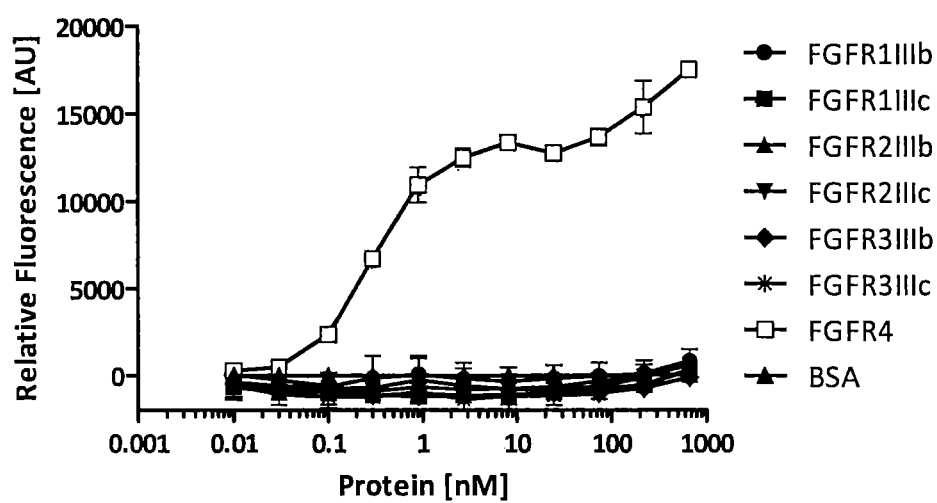
FIG. 5 is a graph showing binding of the human antibody U4-3 to different FGF receptors. As can be seen the antibody U4-3 recognizes human FGFR4 with high specificity and does not cross-react with other members of the FGFR family.

Nunc MaxiSorp® flat-bottom 96 well ELISA plates purchased from Thermo Fisher Scientific were coated with recombinant human FGFR (or BSA as control) as indicated (extracellular domain, Fc chimera) acquired from R&D Systems at a final concentration of 100 µg/well and processed according to manufacturer's instructions. After incubation with anti-FGFR4 antibody U4-3 as indicated, binding was detected with an alkaline-phosphatase coupled goat anti-human IgG F(ab') using the AttoPhos® AP Fluorescent Substrate System purchased from Promega and detected with the Fluostar Omega fluorescent plate reader from BMG Labtech. The results are shown in FIG. 5.

The antibody U4-3 recognizes the human FGFR4 with high specificity and—importantly does not cross-react with other members of the FGFR family.

Example 9: Determination of Antibody Binding to Different Extracellular Domains of FGFR4

Figure 6:
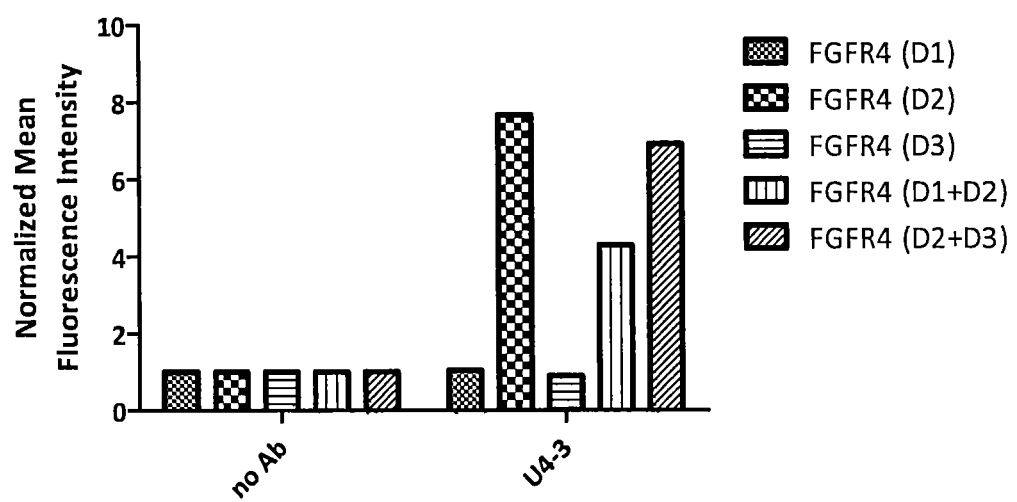
FIG. 6 is a bar graph showing antibody binding to different extracellular domains of FGFR4.

Hek293 cells were obtained from CLS and cultured in DMEM containing 10% FBS under standard conditions at 37° C. and 5% CO2. On Day 0, cells were seeded and after 24 h cells were transfected with plasmids coding for FGFR4 containing the indicated domain. Cells were allowed to express the proteins for 48 h and were then dissociated from the dish with 5 mM EDTA in PBS followed by incubation with indicated anti-FGFR4 antibody. Binding was determined using a Phycoerythrin-conjugated anti-human IgG antibody (Jackson Immuno Research Europe). Data was acquired with a BD Accuri C6 flow cytometer (BD Biosciences) and analyzed using the AccuriC6 software. Binding of U4-3 to FGFR4 occurred mostly at Ig-like domain 2 at the receptor and no binding was observed at Ig-like domains 1 (amino acids 22-180) and 3 (amino acids 249-349). The results are shown in FIG. 6.

Example 10: Determination of Binding Epitope of FGFR4

Figure 7:
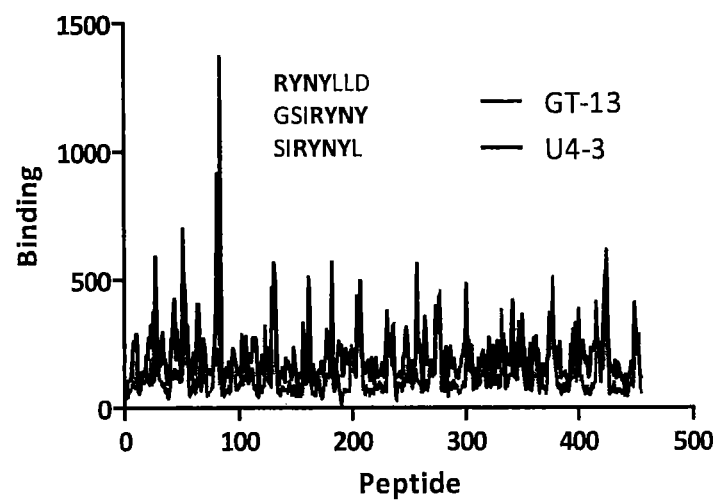
FIG. 7 is a graph showing the determination of the binding epitope of FGFR4 for the antibodies U4-3 and GT-13. It can be seen that highlighted tetra-peptide sequence RYNY (SEQ ID NO: 69) is recognized by U4-3 but not by GT-13.

Peptides were synthesized based on the amino acid sequence of the target protein (domain 2 of human FGFR4 extracellular domain) using standard Fmoc-chemistry and deprotected using trifluoric acid with scavengers. The constrained peptides were synthesized on chemical scaffolds in order to reconstruct conformational epitopes, using Chemically Linked Peptides on Scaffolds (CLIPS) technology. The side-chains of the multiple cysteines in the peptides were coupled to CLIPS templates by reacting onto polypropylene PEPSCAN cards (455 peptide formats/card) with a 0.5 mM solution of CLIPS template such as 1,3-bis (bromomethyl) benzene in ammonium bicarbonate (20 mM, pH 7.9)/acetonitrile (1:1(v/v)). The cards were gently shaken in the solution for 30 to 60 min while completely covered in solution. Finally, the cards were washed extensively with excess of $H_2O$ and sonicated in disrupt-buffer containing 1% SDS/0.1% β-mercaptoethanol in PBS (pH 7.2) at 70° C. for 30 min, followed by sonication in $H_2O$ for another 45 min. The binding of antibody to each peptide is tested in a PEPSCAN-based ELISA. The 455-well credit card format polypropylene cards containing the covalently linked peptides were incubated with primary antibody solution for example consisting of 1 µg/ml diluted in blocking solution, for example 4% horse serum, 5% ovalbumin (w/v) in PBS/1% Tween. After washing (3×10 min), the peptides were incubated with a 1:1000 dilution of antibody peroxidase conjugate for 1 h at 25° C. (or streptavidin-HRP). After washing (3×10 min), the peroxidase substrate 2,2'-azino-di-3-ethylbenzthiazoline sulfonate (ABTS) and 2 µl of 3% $H_2O_2$ were added. After one hour, the color development were measured and quantified with a charge coupled device (CCD)—camera and an image processing system. FIG. 7 shows differences in peptide recognition by the tested antibodies; in particular highlighted tetra-peptide sequence RYNY (SEQ ID NO: 69) is recognized by U4-3 but not by GT-13.

Example 11: Alanine Scanning Mutagenesis FGFR4 Extracellular Domain

Hek293 cells were obtained from CLS and cultured in DMEM containing 10% FBS under standard conditions at 37° C. and 5% $CO_2$. On Day 0, cells were seeded at $2 \times 10^5$ cells/60 mm dish. After 24 h, cells were transfected with 4.8 µg of a plasmid coding for the extracellular domain 2 (D2) of the FGFR4 (Table 7). The expressed proteins carried a flag-tag and differed in the amino acid sequence as described below. Cells were allowed to express the protein for 60 h (with media change in between) and were finally dissociated from the dish with 5 mM EDTA in PBS. Cells were incubated with indicated concentrations of anti-FGFR4 antibody U4-3 and binding was determined using a Phycoerythrin-conjugated anti-human IgG antibody (Jackson Immuno Research). Data was acquired with a BD Accuri C6 flow cytometer (BD Biosciences) and analyzed using the AccuriC6 software. The fluorescence intensity was normalized to the expression of the flag tag. The results are shown in FIG. 8.

The binding of FGFR4 was highly specific and single amino acid mutagenesis in the D2 domain resulted in significantly decreased binding.

TABLE 7

DNA constructs for single amino acid mutagenesis

| Construct No.: | Description/sequence |
|---|---|
| 1 | pCMV-Flag-FGFR4D2-RYNY (WT) |
| 2 | pCMV-Flag-FGFR4D2-AYNY |
| 3 | pCMV-Flag-FGFR4D2-RANY |
| 4 | pCMV-Flag-FGFR4D2-RYAY |
| 5 | pCMV-Flag-FGFR4D2-RYNA |
| 6 | pCMV-Flag-FGFR4D2-G165A |

Example 12: Inhibition of Ligand Binding by Anti-FGFR4 Antibodies

Nunc MaxiSorp® flat-bottom 96 well ELISA plates purchased from Thermo Fisher Scientific were coated with recombinant human FGFR4 (extracellular domain, Fc chimera; acquired from R&D Systems at a final concentration of 4 µg/well and processed according to manufacturer's instructions. Each well was incubated with 1.2 µg/ml of recombinant FGF-19 from R&D Systems, followed by treatment with indicated concentration of anti-FGFR4 antibody U4-3. After incubation and washes, bound FGF-19 was detected with 0.2 µg/ml of biotinylated anti-FGF19 antibody (R&D Systems) followed by incubation with alkaline-phosphatase conjugated Streptavidin. Enzymatic reaction was triggered by incubation with the AttoPhos® AP Fluorescent Substrate System (Promega and detected with the Fluostar Omega fluorescent plate reader from BMG Labtech. The data show that U4-3 is able to effectively compete the binding of FGF-19 to the receptor. The results are shown in FIG. 9.

Example 13: Inhibition of b-FGF-Induced ERK Phosphorylation by U4-3

L6 cells (ATCC) stably expressing full-length human FGFR4 were plated into 12-well dishes (1×10$^5$ cells/well) using DMEM containing 10% FBS under standard tissue culture conditions (37° C., 5% $CO_2$). The next day, the media was replaced with growth media containing indicated concentrations of anti-FGFR4 or control antibodies. After 1 h, b-FGF (R&D Systems) was added at a concentration of 20 ng/ml to indicated wells. After incubation for 10 min, wells were quickly washed with cold PBS before they were lysed in buffer containing Phosphatase (Merck, Darmstadt, Germany) and Protease (Roche, Basel; Switzerland) inhibitors. Samples were finally subjected to Gel Electrophoresis followed by immunoblotting (onto nitrocellulose membranes) using antibodies against ERK and phospho-ERK from Cell Signaling (Danvers, Mass.; U.S.A.). Bands were detected and quantified using the Odyssey detection instrument from Li-Cor (Lincoln, Nebr.; U.S.A.) together with appropriate, fluorescently labeled secondary antibodies. Bands were quantified with the Odyssey software and plotted as a ratio between pERK and total ERK intensity. FIG. 10(A) shows a representative immunoblot and 10(B) the subsequent quantified data. U4-3 shows a concentration-dependent inhibition of b-FGF mediated ERK phosphorylation.

Example 14: Inhibition of Endogenous FGFR4 Phosphorylation by Incubation with U4-3 Antibody Huh-7 cells (obtained from JCRB Cell Bank), cultured in DMEM containing 10% FBS under standard conditions at 37° C. and 5% $CO_2$, were seeded into 60 mm dishes (2×10$^5$ cells per dish). The next day media was removed and replaced with growth media containing anti-FGFR antibody U4-3 (0.1, 1, 3 and 10 µg/ml) or control IgG as indicated. After 6 days, cell were washed twice with PBS and lysed in IP Lysis buffer (containing Phosphatase Inhibitor from Merck and Protease Inhibitor from Roche). Total FGFR4 was immunoprecipitated using an anti-FGFR4 antibody (mouse) and rProtein A Sepharose Fast Flow matrix from GE Healthcare Bio-Sciences. The matrix was washed and samples were finally separated by electrophoresis. Proteins were transferred from gels to nitrocellulose membranes and blotted with antibodies recognizing phosphorylated Tyrosine residues (detection of pFGFR4) or with an antibody recognizing total FGFR4 (Santa Cruz Dallas, Tex.; U.S.A.) to ensure equal loading of the samples. Bands were detected using the appropriate secondary antibodies and the Odyssey detection instrument from Li-Cor. A representative scan is shown for the immunoprecipitation in FIG. 11(A) and the immunoblot of whole cell lysates in FIG. 11(B). After the bands were scanned, the ratio between FGFR4 and pFGFR4 was determined with the Odyssey software and normalized to IgG control values as can be seen in FIG. 11(C). Anti-FGFR4 antibody U4-3 showed strong inhibition of FGFR4 phosphorylation at all concentrations tested.

Example 15: NIH3T3 Spheroid Growth Assay

NIH3T3 cells stably expressing human FGFR4 and human FGF19 were cultured in RPMI1640 containing 10% FBS, 500 µg/ml G418 and 150 µg/ml Hygromycin. At the first day of the experiment, 2,000 cell were seeded into each well of a 96-well PrimeSurface Plate (Sumitomo Bakelite, Tokyo; Japan) containing the indicated concentration of U4-3 or U4-9 antibody. After 5 days incubation in a standard tissue culture incubator (37° C. and 5% $CO_2$), cell growth was determined with the CellTiter-Glo® Luminescent Cell Viability Assay (Promega) using a VICTOR plate reader from Perkin Elmer (Waltham, Mass.; U.S.A.). Values were normalized to untreated samples and both antibodies effectively reduced cell growth more than 70%. IC50 values were calculated and were determined to be 24.7 nM and 10.6 nM (U4-9), respectively. The results are shown in FIG. 12.

Example 16: Inhibition of Soft Agar Colony Growth in Huh-7 Liver Cancer Cells

Huh-7 cells (JCRB Cell Bank) were cultured in DMEM containing 10% FBS under standard conditions at 37° C. and 5% $CO_2$. Cells were harvested with PBS/0.05% Trypsin and resuspended in top agar media (Iscove's Modified Dulbecco's Medium (IMDM), 0.4 agar, 20% FBS) and carefully put on solidified bottom agar media (0.75% agar, 20% FBS in IMDM). Each well of a 96-well plate contained 2,000 cells. The wells were incubated in the presence of anti-FGFR4 antibody U4-3 (highest concentration 30 µg/ml) or control IgG antibody; colony formation was observed over time (approx. 3 weeks). Viable cells were stained using MTT reagent from Sigma (St. Louis, Mo.; U.S.A.) and colonies were quantified using the colony counter system from Oxford Optronix (Abingdon; UK) and normalized to untreated control. The tested anti-FGFR4 antibody U4-3 showed a concentrationdependent growth inhibition of Huh-7 cells when compared to control antibody. The results are shown in FIG. 13.

Example 17: ZR-75-1 Breast Cancer Cell Growth Assay

ZR-75-1 cells (CLS) were cultured in RPMI1640 supplemented with 10% FBS, 10 µg/ml Insulin and 2 mM Glutamine. At the day of the experiment, 2,000 cells were seeded into each well of a 6-well plate in media containing the indicated amount of antibody. Cells were cultured for a total of 16 days (37° C. and 5% $CO_2$) with media and antibody change twice weekly. The media was finally removed and cells stained with 0.5% crystal violet solution (Carl Roth, Karlsruhe, Germany). Visible colonies were counted with the colony counter system (Oxford Optronix) and normalized to wells which did not receive any treatment (NT). The results are shown in FIG. 14. U4-3 effectively inhibited the formation of visible colonies by approx. 50% when compared to the control treatment.

Example 18: MG-63 Osteosarcoma Spheroid Growth Assay

One thousand MG-63 cells (ATCC) cultured in MEM (10% FBS) were seeded into each well of a 96-well Prime-Surface Plate (Sumitomo Bakelite) containing the indicated amount of antibody. After 5 days incubation in a standard tissue culture incubator (37° C. and 5% $CO_2$), cell growth was determined with the CellTiter-Glo® Luminescent Cell Viability Assay (Promega) using a VICTOR plate reader from Perkin Elmer. The results are shown in FIG. 15.

Antibody U4-3 reduced cell growth about 25%; this was already observed at a concentration of 0.4 μg/ml.

Example 19: In Vivo Inhibition of Huh-7 Tumor Growth

Growth inhibition mediated by anti-FGFR4 antibody in murine tumor model. Female NU/NU Nude mice were obtained from Charles River Laboratories (Boston, Mass.; U.S.A.). Six weeks after birth, animals were subcutaneously injected with 5×10$^6$ Huh-7 cells (in Matrigel, BD Biosciences). 14 days after injection, animals with similar tumor volume were pooled and treated (q3d×3) with anti-FGFR4 antibodies by intraperitoneal injection. The tumor volumes in mm$^3$ were measured at day 15, 18, 21 and 24 after tumor inoculation applying the formula [volume=0.52×(width)$^2$×(length)]. FIG. 16(A) shows a dose-dependent inhibition of tumor growth upon treatment with Huh-7, maximum growth inhibition (approx. 68% was observed at a dose of 25 mpk). At 10 mpk, both U4-3 and U-4-9 showed comparable inhibition of tumor growth (FIG. 16(B)). When U4-3 was directly compared to GT-13 using the same dosing regimen, U4-3 showed superior efficacy and inhibited the tumor growth statistically significant better (FIG. 16(C)).

Example 20: In Vivo Growth Inhibition in Huh-1 and Hep3B Tumor Models

Example A. Growth Inhibition Mediated by Anti-FGFR4 Antibody in Huh-1 Tumor Model Female Balb/c nude mice (5-6 weeks old) were subcutaneously injected with 5×10$^6$ Huh-1 cells. After the tumor size reached 150 mm$^3$, animals treated twice weekly for 3 weeks with anti-FGFR4 antibodies administered by intraperitoneal injection [25 mpk]. The tumor volumes in mm$^3$ were measured as indicated by caliper using the formula (L×W$^2$)/2. The results are shown in FIG. 17(A).

Example B. Growth Inhibition Mediated by Anti-FGFR4 Antibody in Hep3B Tumor Model Animals were treated as above except that Hep3B cells were used and that they were implanted using Matrigel (BD Biosciences). Tumor volumes were determined as described above at indicated times. The results are shown in FIG. 17(B).

Tumor growth was inhibited by U4-3 and—in case of Huh-1cells—the tumor growth inhibition was more than 50%.

Example 21: In Vivo Inhibition of SNU-761 Tumor Growth

Growth inhibition mediated by anti-FGFR4 antibody in another liver murine tumor model.

Female BALB/c nude mice were obtained from Shanghai Lingchang Bio-Technology Co. Ltd (LC, Shanghai, China). Seven weeks after birth, animals were subcutaneously injected with 1×10$^7$ SNU-761 tumor cells in 0.1 ml of PBS (1:1 in Matrigel, BD Biosciences San Jose, Calif.; U.S.A.). Treatment started when the mean tumor size reached 119 m$^3$. Anti-FGFR4 antibody was administered by intraperitoneal injection twice a week for 5 weeks. Since the tumor volume can affect the effectiveness of any given treatment, mice were assigned into groups using randomized block design based on their tumor volumes. This ensured that all the groups had comparable baselines. Using randomized block design to assign experimental animals, ensured that each animal had the same probability of being assigned to any given treatment group and therefore systematic error was minimized. Tumor volumes were measured twice weekly in two dimensions using a caliper, and the volume was expressed in mm$^3$ using the formula: V=0.5 a×b$^2$ where a and b are the long and short diameters of the tumor, respectively.

The tumor volumes in mm$^3$ were measured at days 95 to 130 with a distance of about 3 to 4 days. FIG. 18 shows inhibition of tumor growth of human hepatic SNU-761 carcinoma xenograft cells upon treatment with anti-FGFR4 antibody U4-3. U4-3 demonstrated significant anti-tumor activity at 25 mg/kg dose level in a subcutaneous SNU-761 human hepatic carcinoma xenograft model. Tumor growth inhibition is calculated as % TGI=1−(Ti−T0)/(Vi−V0))*100; Ti as the geometric mean tumor volume of the treatment group on the measurement day; T0 as the geometric mean tumor volume of the treatment group at D1; Vi as the geometric mean tumor volume of control group at the measurement day; V0 as the geometric tumor volume of the control group at D1.

Example 22: In Vivo Efficacy in a Patient-Derived Gastric Xenograft Tumor Model Growth inhibition mediated by anti-FGFR4 antibody in a patient-derived gastric xenograft tumor model GA0080.

Female BALB/c nude mice (age of eight to nine weeks) were obtained from Shanghai Lingchang Bio-Technology Co. Ltd (LC, Shanghai, China). HuPrime® Gastric cancer model GA0080 derived from a female patient was selected for this efficacy study. The pathology of this model is moderately-poorly differentiated adenocarcinoma.

Tumor fragments from stock mice, inoculated with selected primary human gastric tissues, were harvested and used for inoculation into BALB/c nude mice. Each mouse was inoculated subcutaneously at the right flank (2-4 mm in diameter) for tumor development. Treatment started when the average tumor size reached about 153 mm$^3$. Mice were allocated randomly into 2 experimental groups according to their tumor sizes. FGFR4 antibody U4-3 was administered to the tumor-bearing mice from day 1 through day 22 with the schedule of 1, 4, 8, 11, 15, 18, 22. Tumor sizes were measured twice as described above.

FIG. 19 shows inhibition of tumor growth of HuPrime® gastric cancer model GA0080 upon treatment with anti-FGFR4 antibody U4-3. U4-3 demonstrated anti-tumor activity of about 25% in the gastric xenograft model.

Example 23: In Vivo Efficacy in a Human Colon Cancer Xenograft Tumor Model

Growth inhibition mediated by anti-FGFR4 antibody in a human colon cancer (SW620) xenograft tumor model.

Female NMRI nude mice (age of five to six weeks) were obtained from Charles River GmbH (Sulzfeld, Germany). 5×10$^6$ SW620 tumor cells (ATTC No. CCL-227) in 100 μl PBS were inoculated subcutaneously into the left flank of 20 female NMRI nude mice. On day 12, after a mean tumor size of approx. 150-200 mm$^3$ had been reached, 20 tumor-bearing animals were block randomized into 2 groups of 10 animals each according to tumor sizes. Anti-FGFR4 antibody U4-3 was administered twice weekly intraperitoneally to the tumor-bearing mice from day 1 through day 38 with the schedule of 13, 17, 20, 24, 27, 31, 34 and 38. Tumor sizes were measured twice weekly as described above. FIG. 20 shows inhibition of tumor growth upon treatment with anti-FGFR4 antibody U4-3. U4-3 demonstrated a noticeable inhibition of primary tumor growth.

The invention claimed is:

1. An antibody which is directed against an epitope between amino acids 119-248 of human FGFR4, SEQ ID NO: 70, or an antigen binding fragment thereof, said antibody comprising:
   (i) a heavy chain comprising:
      (a) a CDRH1 as shown in SEQ ID NO: 3,
      (b) a CDRH2 as shown in SEQ ID NO: 8, and
      (c) a CDRH3 as shown in SEQ ID NO: 15, and
   a light chain comprising:
      (d) a CDRL1 as shown in SEQ ID NO: 23,
      (e) a CDRL2 as shown in SEQ ID NO: 25, and
      (f) a CDRL3 as shown in SEQ ID NO: 30,
   or
   (ii) a heavy chain comprising:
      (a) a CDRH1 as shown in SEQ ID NO: 3,
      (b) a CDRH2 as shown in SEQ ID NO: 8, and
      (c) a CDRH3 as shown in SEQ ID NO: 15, and
   a light chain comprising:
      (d) a CDRL1 as shown in SEQ ID NO: 68,
      (e) a CDRL2 as shown in SEQ ID NO: 27, and
      (f) a CDRL3 as shown in SEQ ID NO: 35.

2. The antibody of claim 1 comprising a heavy chain variable region as shown in SEQ ID NO: 54 and a light chain variable region as shown in SEQ ID NOs. 62 and 67, or heavy and light chain variable regions differing in one or two amino acids from those shown in SEQ ID NOs. 54, 62 and 67.

3. The antibody of claim 1, which is a Fab fragment, a Fab' fragment, a F(ab'), fragment, a Fv fragment, a diabody, or a single chain antibody molecule.

4. The antibody of claim 1, which is of the IgG1-, IgG2-, IgG3- or IgG4-type.

5. A conjugate comprising an antibody of claim 1, wherein the antibody is coupled to a labeling group or to an effector group.

6. A fusion protein comprising an antibody of claim 1 fused to IL-2.

7. A process of manufacturing an antibody of claim 1, a conjugate thereof coupled to a labeling group or to an effector group, or a fusion protein thereof fused to IL-2, comprising the step of obtaining said antibody, antibody conjugate or fusion protein from a host.

8. A pharmaceutical composition comprising the antibody of claim 1, a conjugate thereof coupled to a labeling group or to an effector group, or a fusion protein thereof fused to IL-2.

9. A kit comprising the antibody of claim 1, a conjugate thereof coupled to a labeling group or to an effector group, or a fusion protein thereof fused to IL-2.

10. The antibody of claim 1, comprising a heavy chain variable region as shown in SEQ ID NO. 54 and a light chain variable region according to SEQ ID NO. 62, or heavy and light chain variable regions differing in one or two amino acids from those shown in SEQ ID NO. 54 and 62.

* * * * *